(12) United States Patent
Albrecht et al.

(10) Patent No.: US 8,636,751 B2
(45) Date of Patent: Jan. 28, 2014

(54) METHODS AND DEVICES FOR THE REROUTING OF CHYME TO INDUCE INTESTINAL BRAKE

(75) Inventors: Thomas E. Albrecht, Cincinnati, OH (US); Jeffrey L. Aldridge, Lebanon, OH (US); Sean P. Conlon, Loveland, OH (US); Michael S. Cropper, Edgewood, KY (US); Denzel Z. Herrera-Davis, Cincinnati, OH (US); Daniel F. Dlugos, Jr., Middletown, OH (US); Jason L. Harris, Mason, OH (US); Christopher J. Hess, Cincinnati, OH (US); Kevin L. Houser, Springboro, OH (US); Mario Gutierrez, Loveland, OH (US); Prasanna Malaviya, Mason, OH (US); Amy L. Marcotte, Mason, OH (US); Jeffrey D. Messerly, Cincinnati, OH (US); Anthony Nguyen, West Chester, OH (US); Mark S. Ortiz, Milford, OH (US); Mark D. Overmyer, Cincinnati, OH (US); Alessandro Pastorelli, Rome (IT); Galen C. Robertson, Durham, NC (US); Frederick E. Shelton, IV, Hillsboro, OH (US); Michael J. Stokes, Cincinnati, OH (US); Foster B. Stulen, Mason, OH (US); James W. Voegele, Cincinnati, OH (US); Lauren S. Weaner, Cincinnati, OH (US); Tamara S. Vetro Widenhouse, Clarksville, OH (US); James A. Woodard, Jr., Mason, OH (US); Mark S. Zeiner, Mason, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 272 days.

(21) Appl. No.: 13/104,192

(22) Filed: May 10, 2011

(65) Prior Publication Data

US 2011/0295055 A1    Dec. 1, 2011

Related U.S. Application Data

(60) Provisional application No. 61/348,267, filed on May 26, 2010.

(51) Int. Cl.
*A61B 17/10*    (2006.01)

(52) U.S. Cl.
USPC ........................................... 606/139

(58) Field of Classification Search
USPC .................... 606/139, 144–150, 222–233
See application file for complete search history.

(56) References Cited

U.S. PATENT DOCUMENTS

| 4,665,917 A | 5/1987 | Clanton et al. |
| 4,703,887 A | 11/1987 | Clanton et al. |

(Continued)

OTHER PUBLICATIONS

U.S. Appl. No. 11/958,368, filed Dec. 18, 2007, Marcotte et al.

(Continued)

*Primary Examiner* — Melanie Tyson
(74) *Attorney, Agent, or Firm* — Frost Brown Todd LLC

(57) ABSTRACT

Methods and devices reroute chyme to induce intestinal brake in order to improve the effectiveness of bariatric surgical procedures and to improve comorbidity resolution. A bowel is manipulated to provide a shortened path for chyme to travel to the ileum. These methods and devices of rerouting chyme to induce intestinal brake may include one or more of a surgical procedure, an implanted device, or a combination of an implant with an improved surgical procedure.

5 Claims, 63 Drawing Sheets

(56) References Cited

U.S. PATENT DOCUMENTS

| | | |
|---|---|---|
| 5,188,636 A | 2/1993 | Fedotov |
| 5,242,457 A | 9/1993 | Akopov et al. |
| 5,484,451 A | 1/1996 | Akopov et al. |
| 5,573,543 A | 11/1996 | Akopov et al. |
| 6,543,456 B1 | 4/2003 | Freeman |
| 7,115,136 B2 | 10/2006 | Park et al. |
| 7,309,341 B2 | 12/2007 | Ortiz et al. |
| 7,452,363 B2 | 11/2008 | Ortiz |
| 8,123,765 B2 | 2/2012 | Deem et al. |
| 8,221,439 B2 | 7/2012 | Dlugos, Jr. et al. |
| 2004/0133147 A1 | 7/2004 | Woo |
| 2006/0036267 A1* | 2/2006 | Saadat et al. .................. 606/153 |
| 2006/0271075 A1 | 11/2006 | Bilotti et al. |
| 2007/0175488 A1 | 8/2007 | Cox et al. |

OTHER PUBLICATIONS

U.S. Appl. No. 12/027,784, filed Feb. 7, 2008, Dlugos, Jr. et al.
U.S. Appl. No. 12/027,817, filed Feb. 7, 2008, Dlugos, Jr. et al.
International Search Report dated Jul. 20, 2012 for Application No. PCT/US2011/037657.
U.S. Appl. No. 61/348,267, filed May 26, 2010.

* cited by examiner

METHODS AND DEVICES FOR THE REROUTING OF CHYME TO INDUCE INTESTINAL BRAKE

PRIORITY

This application claims priority to U.S. Provisional Patent Application Ser. No. 61/348,267, entitled "Methods and Devices for the Rerouting of Chyme to Induct Intestinal Brake," filed May 26, 2010, the disclosure of which is incorporated by reference herein.

FIELD OF THE INVENTION

This invention relates to methods and devices for the rerouting of chyme to induce intestinal brake.

BACKGROUND OF THE INVENTION

Obesity is the accumulation of excess body fat on a person to the extent it may have an adverse effect on health and is a leading, preventable cause of death worldwide. Adverse health effects due to obesity, which are a consequence of the mechanical or metabolic effects of obesity, range from mild to acute and often include development of comorbidities. These comorbidities include cardiovascular disease, diabetes and degenerative diseases of the cartilaginous tissue between the vertebral bones of the spine and other weight bearing joints. Treatment for mild cases includes dietary and physical exercise and severe cases require surgery. Bariatric surgery is a term encompassing all of the surgical treatments for morbid obesity. Every year there are more morbid obese and those who do seek bariatric surgery are heavier.

Meal digestion and absorption are time-intensive processes and bariatric procedures effectively reduce stomach volume and or bowel length and operate to promote earlier satiation, a perception colloquially referred to as 'feeling full'. Inducing this feeling results in loss of desire to continue eating and a resulting reduction in caloric intake. Chyme is a semi-fluid mass of mechanically and chemically digested food which is produced by the stomach and expelled into the duodenum where it begins the journey through the gastrointestinal (GI) tract. To optimize digestion and absorption, transit of the meal through the GI tract is regulated by a complex integration of signals from the small intestine in response to nutrient sensing in the bowel or gut. Satiation results from signals originating in the stomach caused by distension and signals generated by the jejunal brake and ileal brake. Activation of the distal part of the gut, the so called ileal brake, leads to reduction in hunger and food intake. Collectively, the jejunal brake response and ileal brake response are referred to as intestinal brake.

Intestinal brake has been shown to initiate satiation more quickly and is theorized to play an important role in the effectiveness of bariatric surgical procedures such as Roux-en-Y gastric bypass (RYGB) and has shown both excess weight loss (EWL) and comorbidity resolution. Bariatric procedures such as Ileal Transposition have been developed based on the concept of delivery of substances with rich nutrient/caloric content to the ileum in order to trigger the intestinal brake response and have been shown to be effective in numerous animal models. Food reaching the ileum contributes to L-cell stimulation and production of glucagon-like peptide-1 (GLP-1) hormones that signal satiety leading to the cessation of hunger and a corresponding loss of desire to eat. Transposition of the terminal ileum to the duodenum provides GLP-1 whenever glucose is ingested. The presence of fat or glucose in the duodenum or the ileum has shown to increase GLP-1. Also known as the "ileal-brake" hormone, GLP-1 slows down or stops emptying of the stomach and slows motility of the small bowel thus promoting earlier satiation and increasing the effectiveness of bariatric procedures.

Accordingly, there remains a need for methods and devices of rerouting chyme to induce intestinal brake in order to improve the effectiveness of bariatric surgical procedures and to improve comorbidity resolution.

DETAILED DESCRIPTION

The following description contains embodiments of methods and devices for rerouting chyme in order to induce intestinal brake and facilitate desired weight loss effects. The chyme is rich in caloric and nutrient content and delivery of the chyme to the ileum triggers the intestinal brake response. Inducing intestinal brake by bunching a section of small bowel shortens the distance chyme has to travel through the small bowel.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Figure 1:
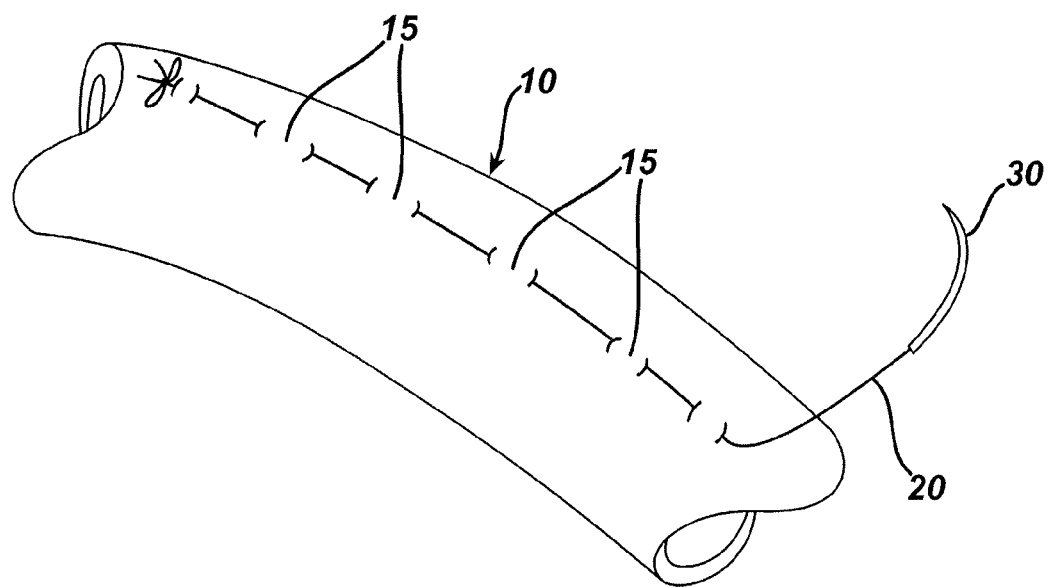
FIG. 1 is a view of a portion of a bowel prior to being bunched.
Figure 2:
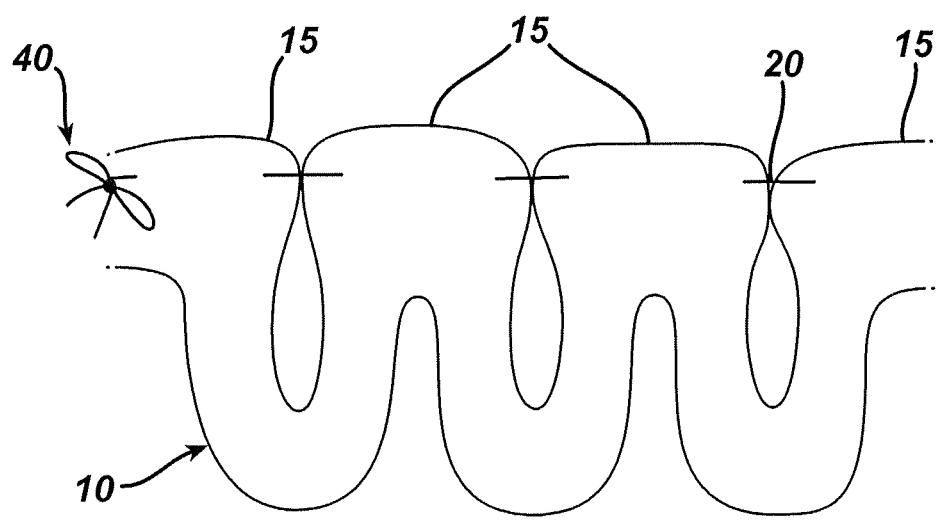
FIG. 2 is a schematic view of the bowel after it is bunched along the suture.

Referring to the Figures, wherein like numerals indicate like or corresponding parts throughout the several views, a segment of a small bowel is shown as 10 in FIG. 1. The bunching of the bowel 10 is achieved by using a suture 20 passed through an outer layer 15 of the bowel 10 using a needle 30. Preferably, as in FIG. 1, needle 30 is used to pass the suture 20 through the outer layer 15 of the bowel 10 in an alternating fashion. As shown in FIG. 2 the ends of suture 20 are drawn together into a knot 40 forming a tight loop causing the bowel 10 to bunch along the suture 20. It is contemplated for suture 20 placement to be accomplished using known surgical techniques or the bunching could be created non-invasively using a flexible endoscope outfitted with a stitching device. It is further contemplated that multiple strands of suture could be used to tailor the bunching of the bowel 10 to create even bunching along the bowel. It is also contemplated that multiple lines of suture may be made. It may be appreciated that other soft tissue clamping devices could be used in place of the suture 20. Examples which may be used to pull the bunch together include staples, clips, clamps or t-tags with sutures attached.

Figure 3:
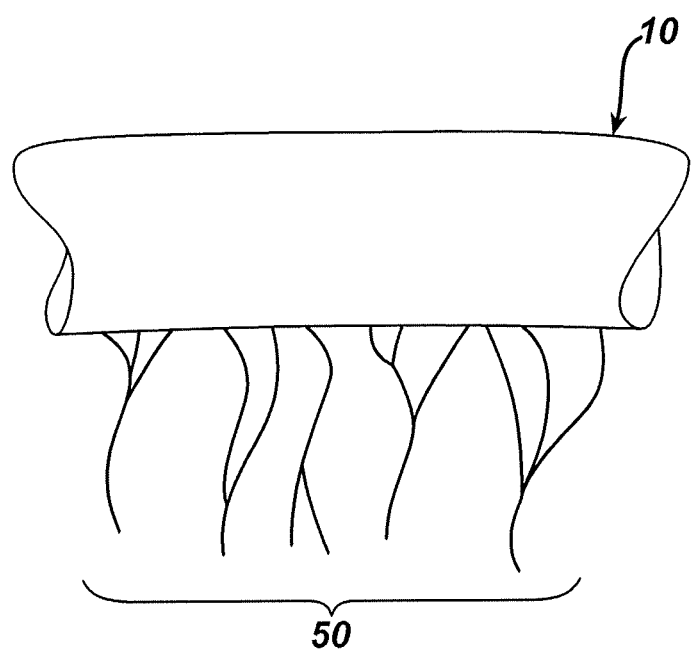
FIG. 3 is a side view of a segment of small bowel prior to intussusception.
Figure 4:
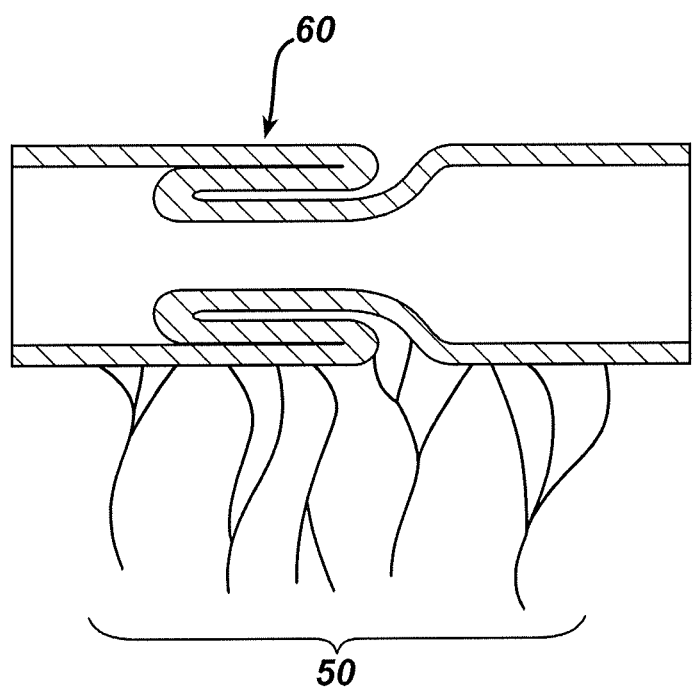
FIG. 4 is a cutaway, side view of a portion of intussuscepted bowel.
Figure 5:
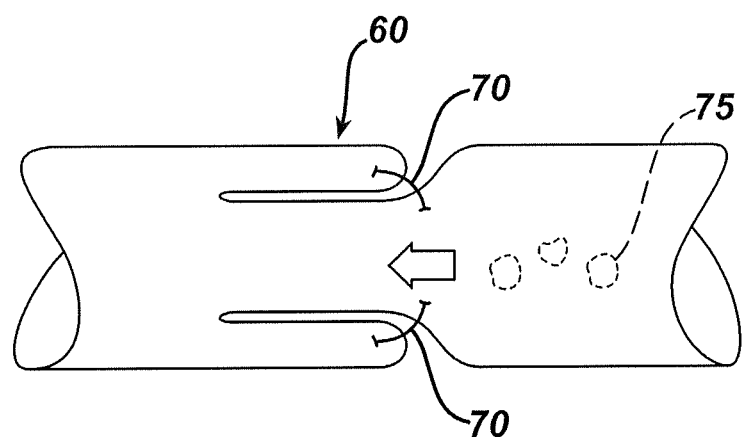
FIG. 5 is a side view of a portion of intussuscepted bowel.

An alternative technique for bunching the bowel 10 involves in-vaginating part of the small intestine into and adjacent section of intestine using a technique referred to as intussusception as shown in FIGS. 3-5. FIG. 3 shows a plurality of mesenteric veins 50 attached to the segment of small bowel 10 prior to intussusception. Turning to FIG. 4, a portion of intussuscepted bowel 60 is created by causing a portion of bowel to roll over upon itself circumferentially. This may be done repeatedly in discrete lengths to eliminate extensive entrainment of the mesentery. Each portion of intussuscepted bowel 60 is secured using a suture 70 passed through the outer layer 15 of the bowel 10 as shown in FIG. 5.

Combining several of the portions of intussuscepted bowel 60 into a string or series provides an effectively shorter path for the chyme 75 to follow as it passes through the bowel toward the ileum. The result is that the chyme 75, which is nutrient and calorie rich, activates the intestinal brake and leads to reduction in hunger and food intake.

Figure 6:
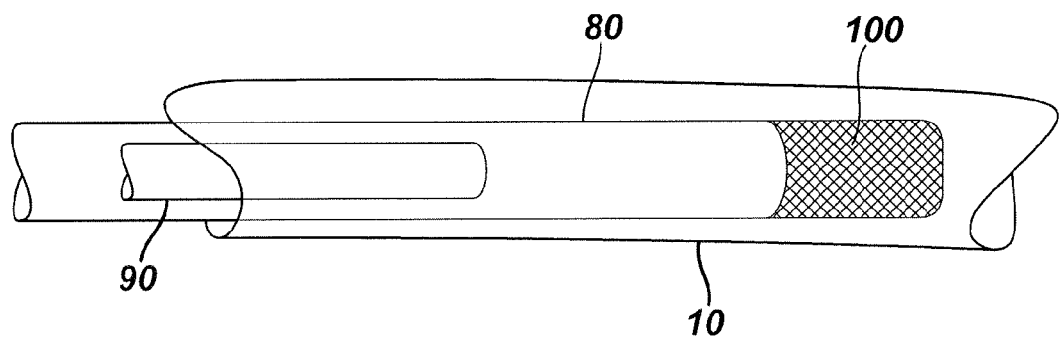
FIG. 6 is a schematic, partially transparent view of an overtube inserted a bowel prior to being bunched.
Figure 7:
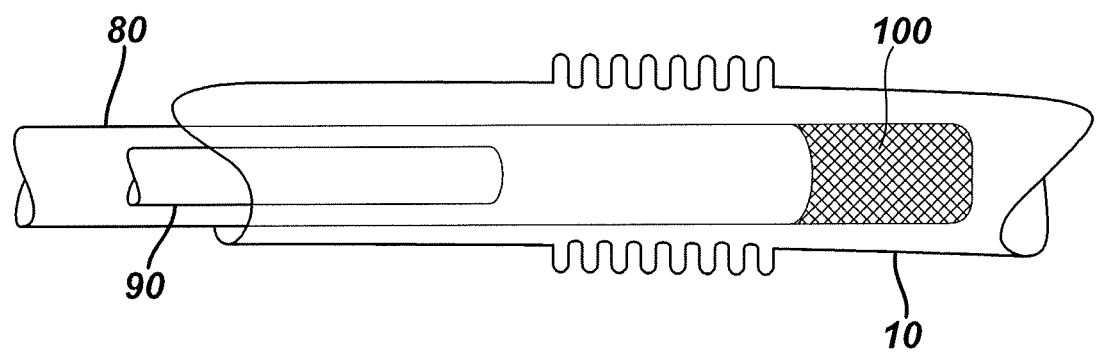
FIG. 7 is a schematic, partially transparent view of the bowel partially bunched.
Figure 8:
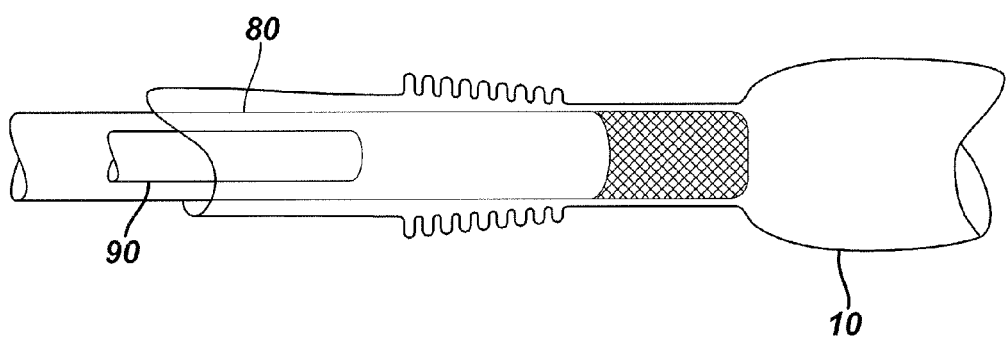
FIG. 8 is a schematic, partially transparent view of the bunched bowel.

FIGS. 6-8, refer to an alternate technique for bunching the bowel. FIG. 6 is a schematic, partially transparent view of the bowel 10. In this embodiment, a tube 80, such as an over tube for an endoscope 90, is advanced longitudinally distal from the endoscope and positioned into the bowel 10. Preferably, the tube 80 includes a suction means 100 at a distal end of the tube 80. Activation of the suction means 100 causes the bowel 10 proximate the distal end of the tube 80 to adhere to the distal end of the tube 80 and bunching of the bowel 10 occurs as the tube is retracted as shown in FIGS. 7 and 8. The bunching is then secured using sutures. The suction means 100 may be used to aid the suturing process. It may be appreciated that other soft tissue clamping devices could be used in place of the suture 20. Examples of devices which may be used to pull the bunch together include staples, clips, clamps or t-tags with sutures attached. Non-limiting disclosures of devices and methods for securing bunched tissue can be found in U.S. Pat. No. 5,242,457 to Akopov et al., U.S. Pat. No. 5,484,451 to Akopov et al., U.S. Pat. No. 4,703,887 to Clanton et al., U.S. Pat. No. 5,188,636 to Fedotov, U.S. Pat. No. 5,484,451 to Akopov et al., U.S. Pat. No. 5,573,543 to Akopov et al., and U.S. Pat. No. 4,665,917 to Akopov et al. are hereby incorporated by reference in its entirety.

Figure 9:
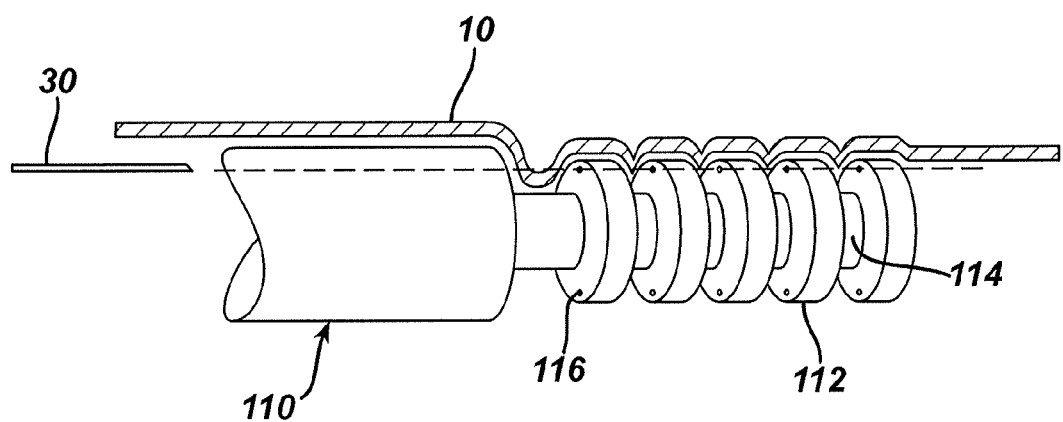
FIG. 9 shows a partial section of bowel having a tube disposed therein.

FIG. 9 shows a partial section of bowel 10 having a tube 110 disposed therein. Preferably, the tube 110 is a vacuum tube which includes a series of circumferential ridges 112 and valleys 114 and suction holes 116 placed advantageously along the length of the tube 110. As shown in FIG. 9 a preferred placement for the suction holes 116 would be in the valleys to draw the tissue about the tubing. The tube 110 could then be secured to the bowel 110 using the needle 30 and suture (not shown). A stitch is formed by passing the needle 30 parallel to the center axis of the tube 110 near the circumference of the tube such that it pierces the bowel 110 tissue which has been drawn in between the valleys 114 and the ridges 112 by the suction holes 116. It may be appreciated that soft tissue clamping devices could be used to secure the bowel 10 to the tube 110 in place of the suture (not shown). Examples which may be used to secure the bowel 10 to the tube 110 include staples, clips, clamps or t-tags with sutures attached.

The bunching effect of this procedure provides an effectively shorter path for the chyme 75 to follow as it passes through the bowel toward the ileum. The result is that the chyme 75, which is nutrient and calorie rich, activates intestinal brake in the distal part of the gut and leads to loss of hunger and an associated reduction in food intake. This procedure, which may be performed endoscopically, enables the proven weight loss effects of an ileal transposition procedure without transecting the bowel lumen thus reducing the surgical risk. Further, bunching of the bowel 10 as described results in less anatomical change when compared to a traditional ileal transposition and has the added benefit of being reversible.

In an alternative embodiment, intestinal brake is induced through bowel lumen size reduction. Chyme transit through the intestine is impacted by reducing the diameter of the bowel lumen locally. In this particular embodiment, a longitudinal firing of a linear cutter across the lumen will result in minor reduction of the lumen diameter. Alternatively, an end to end anastomosis will result in a similar reduction in local lumen size. Both methods slow chyme transit allowing increased duration of release of satiation signal hormones such as peptide YY (PYY) and GLP-1 which inhibit gastric secretion. Preferably, a laparoscopic device is used to create the smaller lumen. For example a small endoscopic stapler may be used to create a very small controllable plication in the lumen.

Figure 10A:
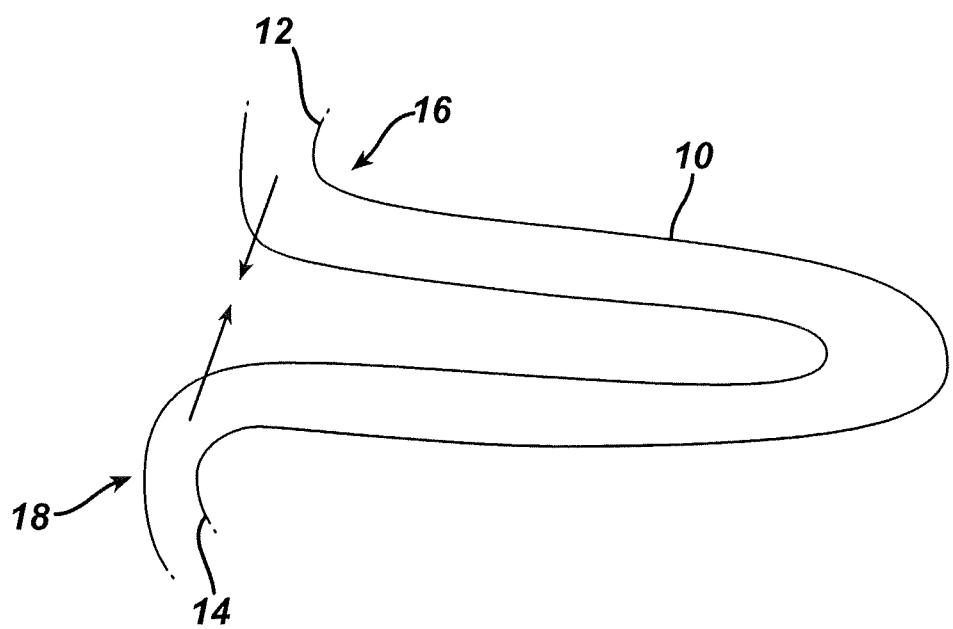
FIG. 10a is a schematic view of a portion of small bowel prior to performance of an ileum brake surgical procedure.
Figure 10B:
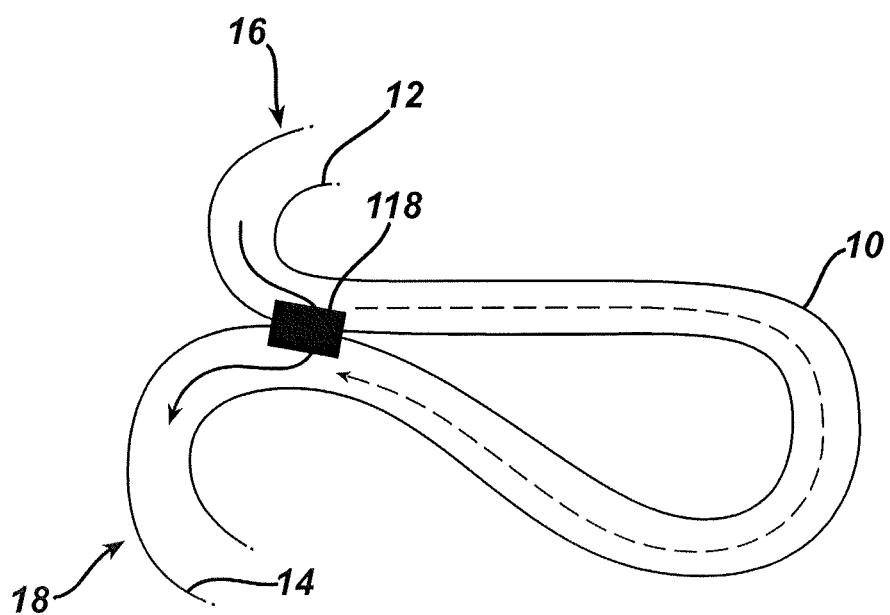
FIG. 10b is a schematic view of an ileum brake formed by an anastomosis of the ileum to the upper jejunum.

FIGS. 10*a*-10*b* show creation of an ileum brake by formation of an anastomosis using an open otomy providing increased satiety through recirculation of digestive nutrients. FIG. 10*a* is a schematic view of a portion of small bowel 10 prior to performance of an ileum brake surgical procedure. The small bowel 10 of FIG. 10*a* includes an opening 12 in an ileal region 16 of the small bowel 10 proximal the pylorus (not shown) and a distal opening 14 in an upper jejunal region 18. Chyme (not shown) from the stomach enters the small bowel 10 through the opening 12 and passes through and exits the small bowel 10 through the distal opening 14. In FIG. 10*b*, an ileum brake formed by an anastomosis of the ileum 16 to the upper jejunum 18 is shown. The anastomosis of the ileum 16 to the upper jejunum 18 to creates a small fistula 118. It may be appreciated that the fistula 118 may be formed using a balloon or wire stent. The fistula 118 allows a small portion of chyme exiting the stomach into the ileum 16 to be diverted to the upper jejunum 18 while the bulk of chyme is processed as normal. As may be appreciated that the ileum brake diverts food which would have a malabsorption aspect proportional to the size of the opening. The diverted portion is not subject to nutrient extraction due to bypassing the bowel 10 which effectively decreases caloric uptake and enables the ileum to signal satiety sooner. In a preferred embodiment, the anastomosis procedure is performed using circular staples.

FIGS. 11-23 show schematic views of novel devices and new laparoscopic hybrid access port gastric sleeve/bypass procedures to achieve a metabolic impact. Gastric sleeving appears to have some of the short term effects of standard of gastric bypass procedures such as the Roux-en-Y. Effects such as an almost immediate post surgical resolution of type II diabetes and very fast sustainable weight loss. However, older similar gastric modifications would suggest that it will not be durable in the long term. As may be appreciated the present invention does present a much simpler and quicker procedure and can be accomplished entirely laparoscopically. There is a need to create a restrictive component only to limit the caloric intake with apparently some non-understood impact to the metabolic level of the body. Additional components such as metabolic changes would better assure the durability of the procedure is more akin to the Roux-en-Y. As may be appreciated, contemplated metabolic changes include malabsorption or transporting fatty acids to the ileum to induce the ileal brake phenomena. Further, the present invention may also be used to enable other bariatric procedures such as a mini gastric bypass (MGB) procedure. Conventional open otomy methods take on average from twelve to thirty six minutes for some surgeons to perform just the gastro jejunal (G-J) anastomosis. The complexity of the procedure is at the edge of most surgeons and it is rarely purely laparoscopic.

The present invention is an alternative to an open otomy and permits creation of an ileum brake with minimally invasive surgical intervention. Further, the procedure of the present invention creates the ileum brake without having to mobilize an ileum section. Benefits of the method of the present invention include simplified procedure steps compared to the Roux-Y gastric bypass but with similar potential durability to Roux-Y. The procedure is a completely laparoscopic procedure using a single incision site using an umbilicus approach. The procedure requires significantly shorter operating time and offers the benefits of potentially less pain and healing time. Both restrictive and metabolic impacts are provided without the malabsorption problems often associated with the Roux-Y and there is no need for vitamin supplements. Although the total procedure is multi-quadrant, the surgical challenges are limited due to only working in one quadrant at a time. The procedure avoids performing an anastomoses procedure on a stricture and the staple lines are more durable since not firing through another staple line. The procedure removes a piece of jejunum to make simple shunt. There is no gastric wound to close due to trans-gastric steps since the sleeve removes the penetrated section.

Figure 11A:
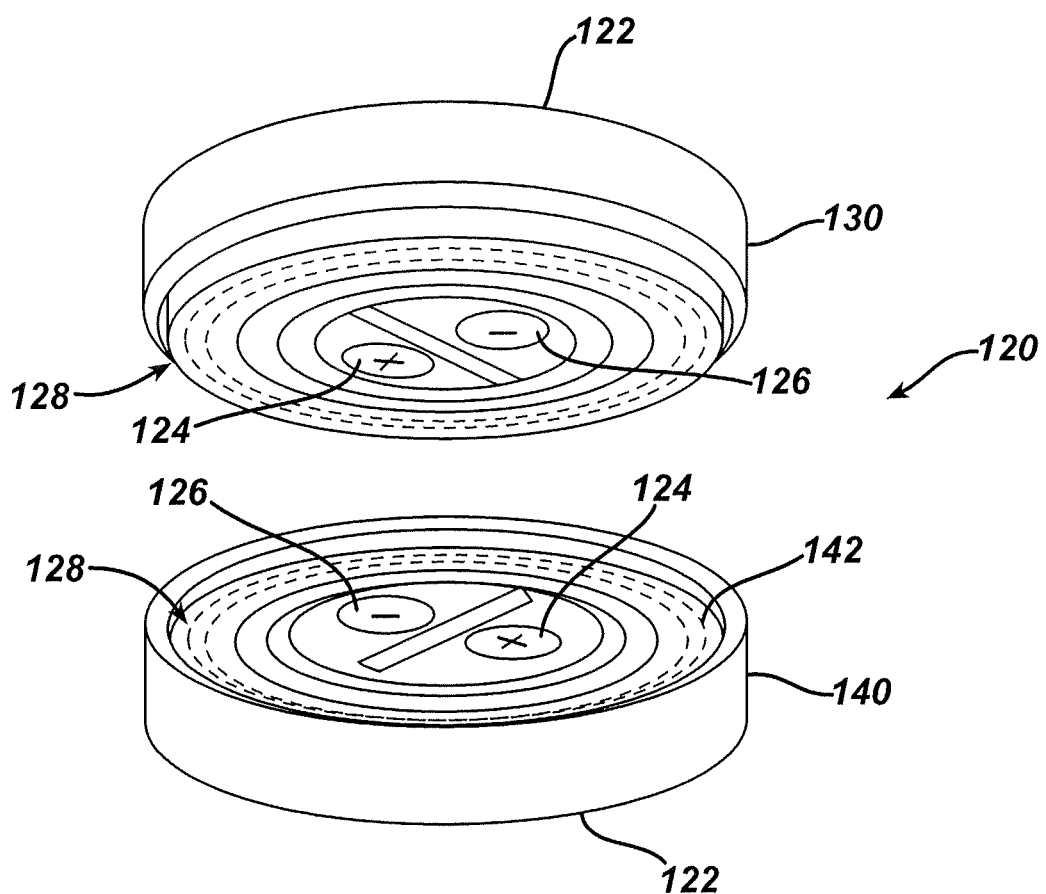
FIG. 11a is a perspective view of a pair of puck anastomosis staples.
Figure 11B:
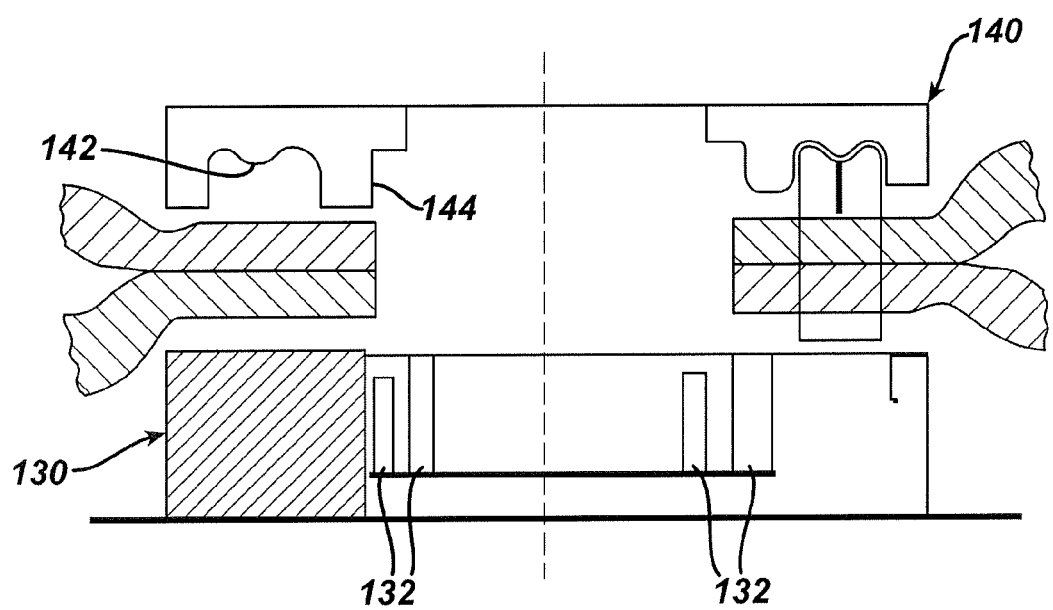
FIG. 11b is a cut away view of the pair of puck anastomosis staples.
Figure 11C:
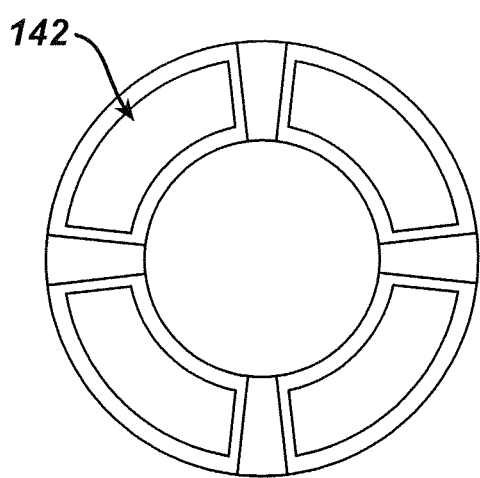
FIG. 11c is a front view of an anvil.

FIG. 11a shows a pair of puck anastomosis staples 120. The individual pucks of the pair of puck anastomosis staples 120 include a cartridge upper half 130 which carries staples 132 and a lower half 140 which carries an anvil 142 and a blade 144 as shown in FIG. 11b. As may be appreciated, it is contemplated that the anvil 142 may be implantable or removable. The anvil 142 may have alternate forms such as having a segmented circumference, as shown in FIG. 11c, to avoid stricture of the stomach or other tissue. It may be appreciated that each of the cartridge upper half 130 has a negative magnetic polarity on the head side 122 and each of the lower half 140 has a negative magnetic polarity on the head side 122 to permit positioning using a magnetic laparoscopic positioner 150 as will be described. The pair of puck anastomosis staples 120 may include absorbable or non-absorbable anastomic rings with the primary function remaining to form an anastomosis. Further, the anastomic rings may be implantable.

Figure 12:
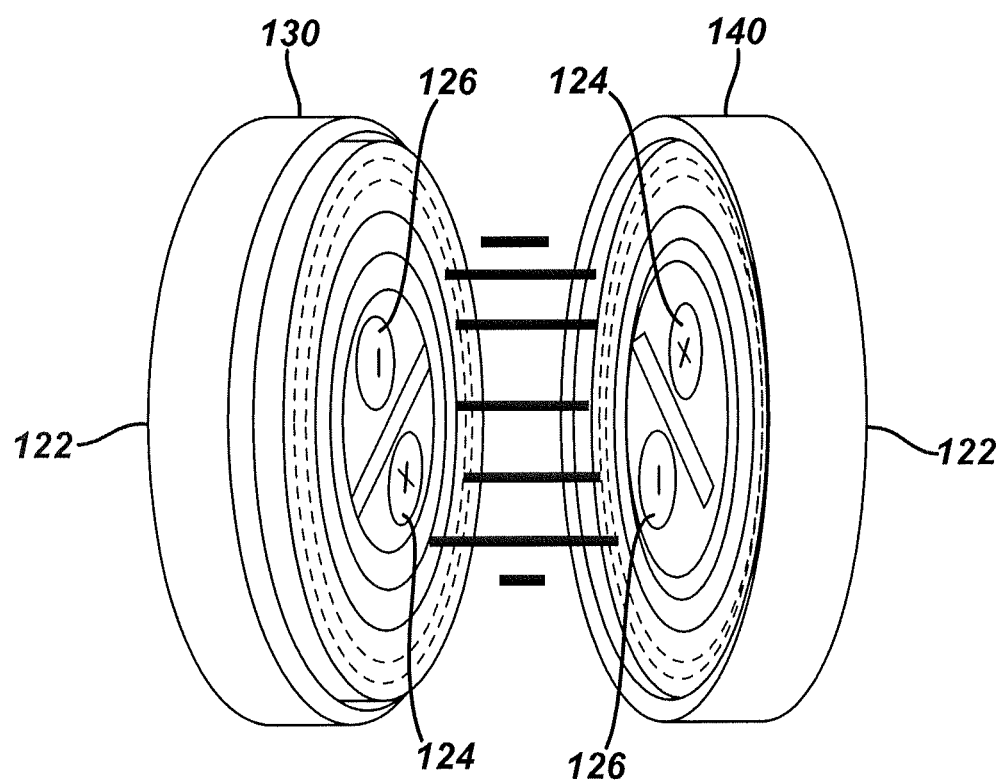
FIG. 12 shows a pair of puck anastomosis staples having internal positive and negative magnets.

FIG. 12 shows a pair of puck anastomosis staples 120 having internal positive 124 and negative 126 magnets imbedded in mating sides 128 opposite the head side of the cartridge upper half 130 and the lower half 140. The internal positive 124 and negative 126 magnets serve to rotate the cartridge upper half 130 and the lower half 140 as will be described. In a preferred embodiment the internal positive 124 and negative 126 magnets are rare earth magnets. However, the internal positive 124 and negative 126 magnets may have alternate forms and it should be understood that the aforementioned rare earth magnets are a non-limiting example and other types of magnets are contemplated without changing or altering the scope of the present invention.

The method for performing the hybrid lap gastric sleeve procedure of the present invention will now be described with reference to FIGS. 13-24. According to a preferred embodiment, the first step includes making a single incision at the umbilicus. Then a flexible retractor (not shown) for a later attached 4-port, single port seal system (not shown) is inserted and secured. In a preferred embodiment, the 4-port system has three 5 mm ports and one 12 mm port. Preferably, the single port seal includes a removable cap.

Figure 13:
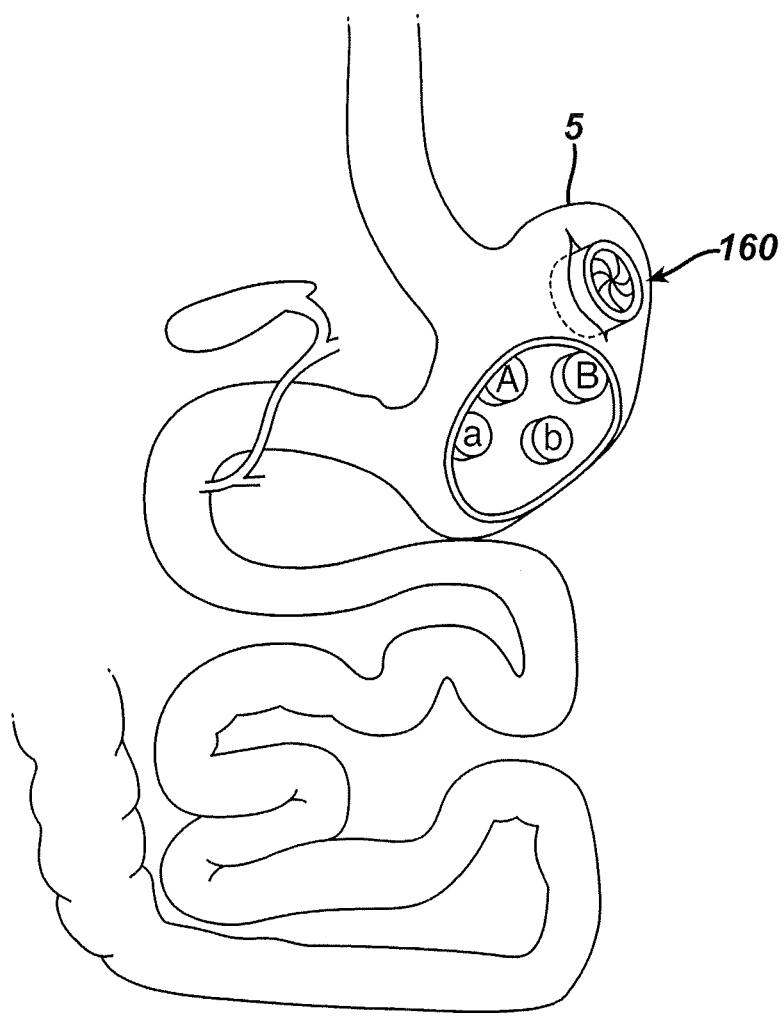
FIG. 13 is a cut away view of a gastrointestinal tract after placement of gastric trocar and placement of a pair of puck anastomosis staples.

Referring to FIG. 13, with the cap of the single port seal system removed, two pairs of the puck anastomosis stapler (two anvil pucks A, B and two cartridge pucks a, b) are inserted into the stomach 5 and a gastric trocar 160 with a dilating iris seal is then positioned as shown. The single port seal cap is then installed and the abdomen is insulfated. In a preferred embodiment, a flexible sleeve gastric trocar retractor is held within the 12 mm deployment shaft and is inserted through the 12 mm port while a 5 mm camera in one of the other 5 mm ports is used for guidance. The flexible sleeve gastric trocar retractor shaft punctures the gastric wall and the flexible retractor is then installed in the gastric wall when the deployment plunger is pressed.

Through the use of two 5 mm graspers, the gastric trocar seal cap is acquired and attached to the gastric trocar, preventing escape of gastric contents into the abdomen. An alternate embodiment uses an insert tool that holds only the flexible retractor ring having the gastric trocar seal cap already installed on the retractor so that no gastric contents are spilled during insertion. The iris seal of the gastric trocar is opened laparoscopically by one of the graspers and the two pairs of puck anastomosis staples 120 are inserted into the stomach and the iris is then closed.

Figure 14:
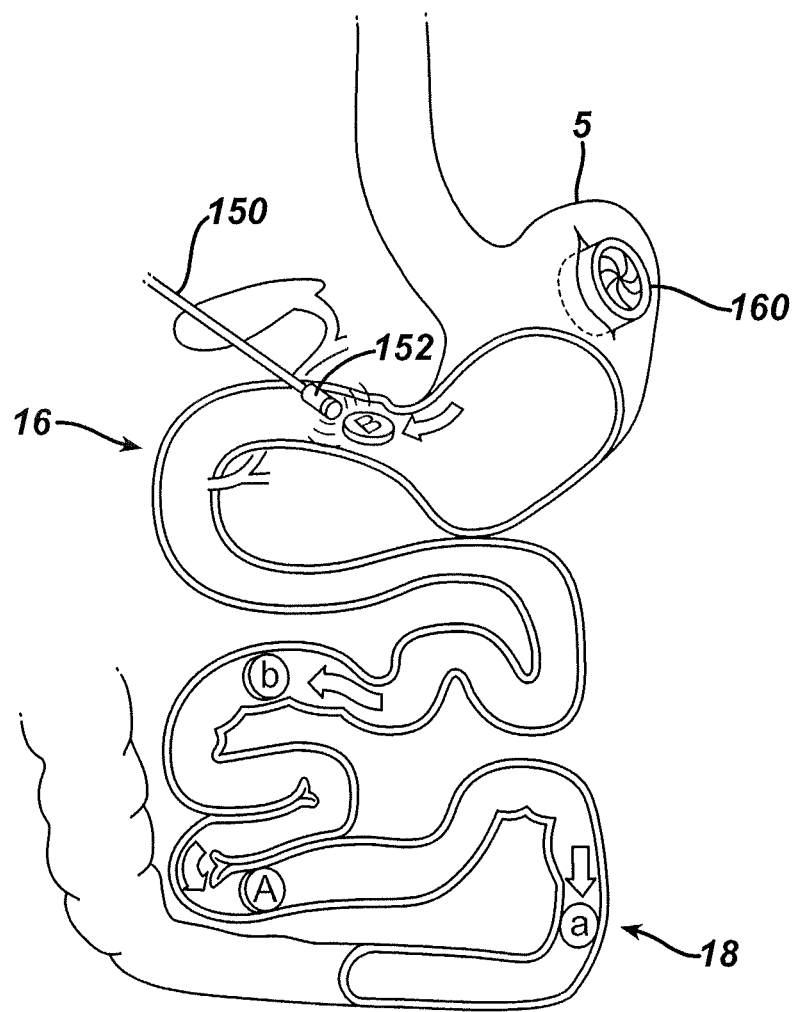
FIG. 14 is a schematic view of a gastrointestinal tract including a gastric trocar seal and two of a pair of puck anastomosis staples.

FIG. 14 shows a schematic view of a gastrointestinal tract including a gastric trocar seal 160 and two of a pair of puck anastomosis staplers 120. As shown in FIG. 14 the individual pucks A, B and a, b of the pair of puck anastomosis staplers 120 are positioned by a magnetic laparoscopic positioner 150. In a preferred embodiment, the pair of puck anastomosis staplers 120 are designed to cut off blood supply to the joining tissue through the magnetic attraction of the individual pucks. Over time the magnetic attraction of the individual pucks causes the tissue to be joined together around the edges resulting in necrosis of the tissue in the center of the puck. The necrotic tissue and the magnetically joined pucks dislodge from the joint area forming a passageway. By this time the anastomosis is completely healed around the edges and the passageway allows food to pass from one side to another. Once dislodged the pucks pass through the GI tract.

In a preferred embodiment, the magnetic laparoscopic positioner 150 is a 5 mm size; however, other sizes are contemplated. In a preferred embodiment, the magnetic laparoscopic positioner 150 has an electromagnetic head 152 that can be switched in polarity to prevent confusing the lower half 140 which carries the anvil 142 and the cartridge upper half 130. In a preferred embodiment, each of the lower halves 140 which carry the anvil 142 have a positive polarity on the head side 122 and the cartridge upper halves 130 have a negative polarity on the head side 122. The magnetic laparoscopic positioner 150 therefore only attracts one or the other cap components depending on the selected polarity of the manipulator.

Figure 15:
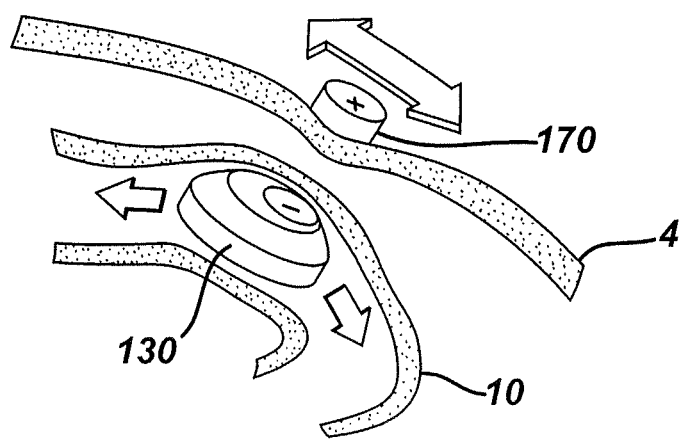
FIG. 15 is a side view of a section of bowel following implantation of the cartridge upper half.

FIG. 15 shows a section of bowel 10 following implantation of the cartridge upper half 130. The cartridge upper half 130 has a negative polarity on the head side 122. When the cartridge upper half 130 is properly positioned, a first holding wafer 170 is inserted through the 12 mm port and is magnetically attached to the cartridge upper half 130 through the jejunum wall. Similarly, a second holding wafer 170 is used to position the lower half 140. Each individual puck of the pair of puck anastomosis staplers 120 is positioned and held in place in a similar fashion. Alternately, the holding wafer 170 may be placed on the abdominal wall 4 as shown in FIG. 15. It is contemplated that each holding wafer 170 includes a means to locate and position the cartridge upper half 130 and the lower half 140 in order to facilitate following the procedure steps. In a preferred embodiment the means to facilitate includes a light source. It is further contemplated that the light source is color coded. The color coding facilitates identification of each holding wafer 170 which is associated with a particular individual puck of the pair of puck anastomosis staplers 120. Further, it is contemplated that the light is a light emitting diode (LED) and the light may flash to aid in locating each holding wafer 170.

Figure 16:
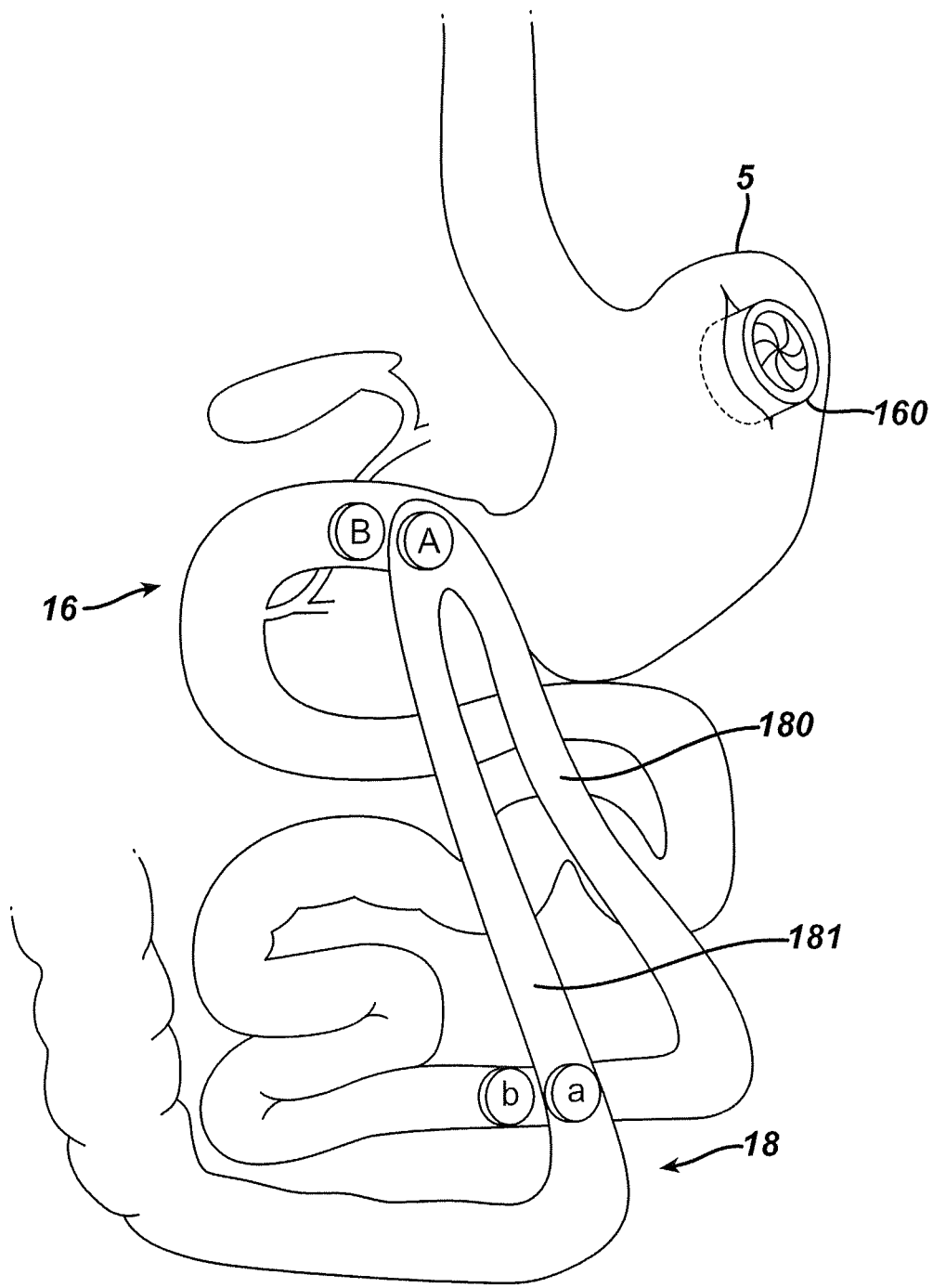
FIG. 16 is a schematic view of a gastrointestinal tract including a gastric trocar seal and where the jejunum is mobilized and two pairs of puck anastomosis staplers are aligned.

FIG. 16 is a schematic view of a gastrointestinal tract including the gastric trocar seal 160 and where the jejunum 180 is mobilized and the two pairs of puck anastomosis staplers A, B and a, b are aligned. Once all four puck anastomosis staplers A, B and a, b are properly positioned the jejunum 180 forms a loop and the puck anastomosis staplers A, B and a, b are mated as shown in FIG. 16. Internal positive 124 and negative 126 magnets are imbedded in mating sides 128 of the cartridge upper half 130 and the lower half 140. The internal positive 124 and negative 126 magnets serve to rotate the cartridge upper half 130 and the lower half 140 within the jejunum 180 to properly orient the cartridge upper half 130 and the lower half 140 when they are adjacent. In a preferred embodiment the internal positive 124 and negative 126 magnets are rare earth magnets. However, as may be appreciated, the internal positive 124 and negative 126 magnets may have alternate forms.

Figure 17:
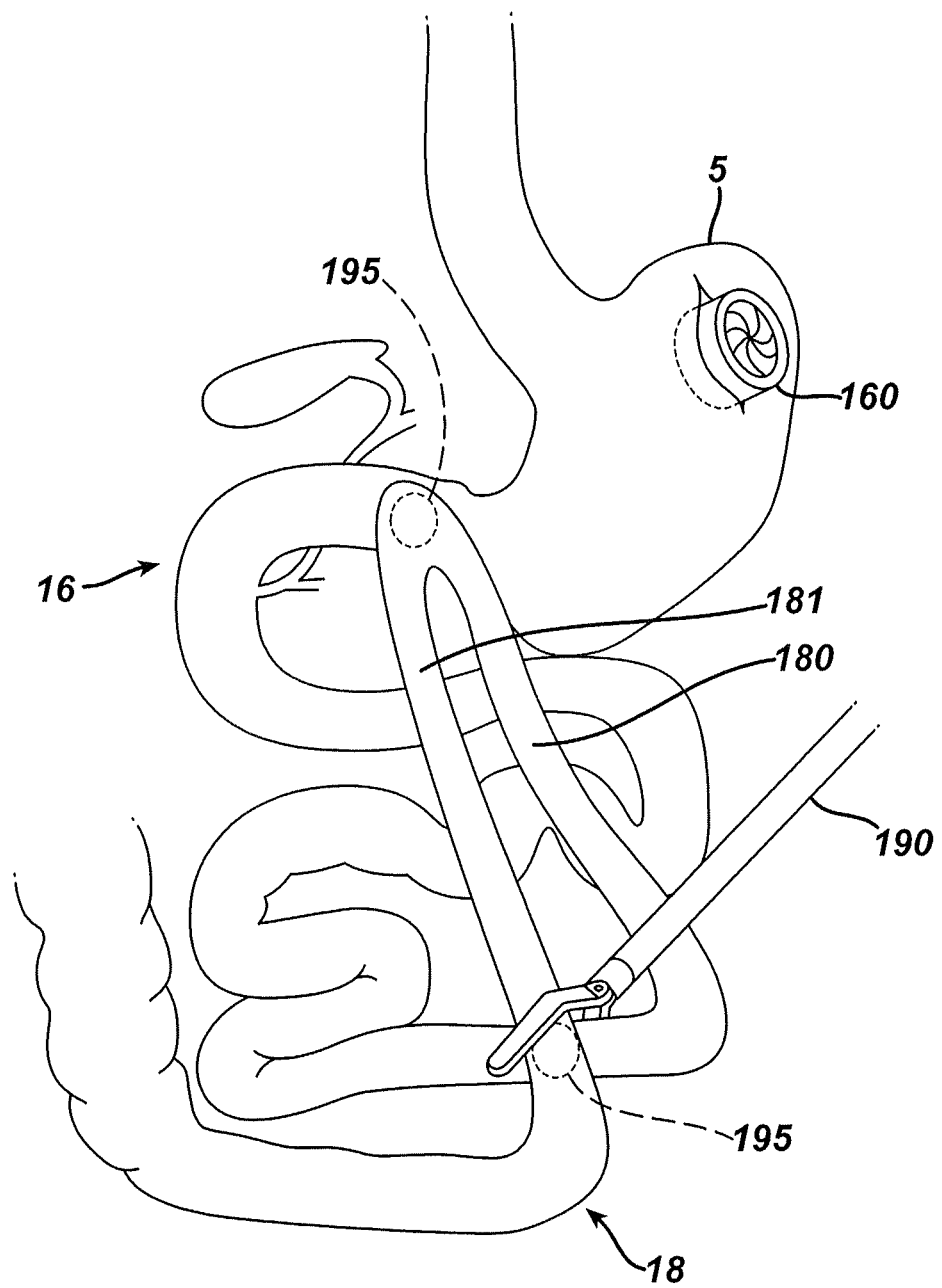
FIG. 17 is a schematic view of a gastrointestinal tract including a gastric trocar seal and where circular compression anastomoses are formed using a laparoscopic firing device between the mobilized jejunum and the ileum and jejunum.

FIG. 17 is a schematic view of a gastrointestinal tract including the gastric trocar seal 160 and where circular compression anastomoses 195 are formed using a laparoscopic firing device 190 between the mobilized jejunum 180 and the ileum 16 and jejunum 18. As shown in FIG. 17, the laparoscopic firing device 190 is exchanged with one of the graspers. It is contemplated that the laparoscopic firing device 190 is merely a larger grasper that cradles the cartridge upper half 130 and the lower half 140 through the jejunum walls. The laparoscopic firing device 190 may have alternate forms such as a four bar linkage or a 12 mm cantilever beam device. The laparoscopic firing device 190 operates to crush the cartridge upper half 130 into the lower half 140 of the pair of puck anastomosis staplers 120. The blade 144 is passed from the cartridge upper half 130 to the lower half 140 at the same time as creating the circular compression anastomosis 195. In a preferred embodiment, the pair of puck anastomosis staplers 120 include covers which are stapled through and create an absorbable buttress for the staple lines. Preferably the covers are made of Vycril to create better strength staple lines as they act as a buttress after deployment. However, the covers may be made of any suitable material.

Figure 18:
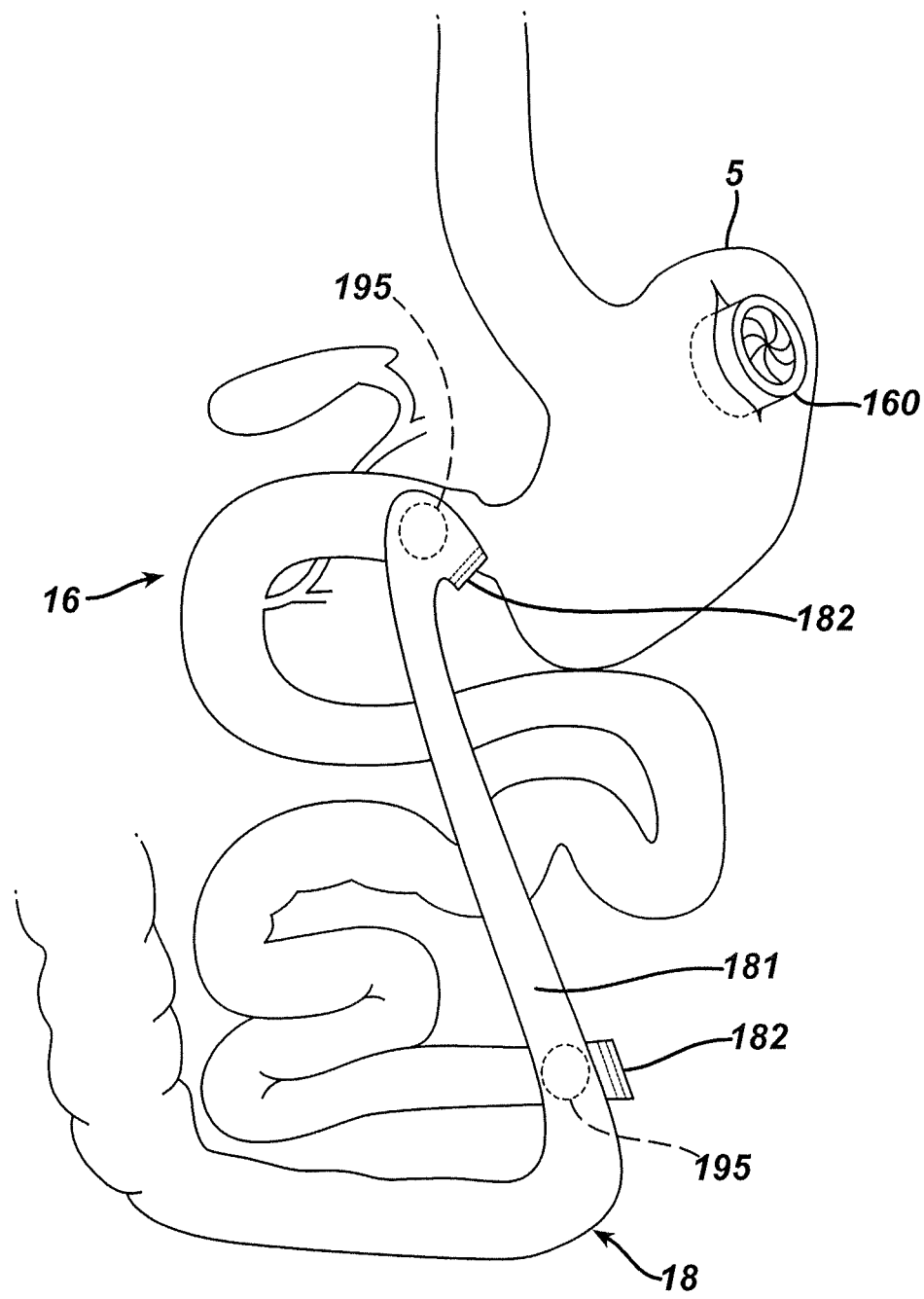
FIG. 18 is a schematic view of a gastrointestinal tract including a gastric trocar seal where circular anastomoses connect and the ileum and jejunum via a jejunum leg.

FIG. 18 is a schematic view of a gastrointestinal (GI) tract including the gastric trocar seal 160 and where circular anastomoses 195 connect and the ileum 16 and jejunum 18 via a jejunum leg 181. Once the pair of puck anastomosis staplers 120 are fired the jejunum now has two full diameter compression anastomoses 195, one near the pyloric sphincter (upper anastomosis 195 in FIG. 18) and one near the ileum (lower anastomosis 195 in FIG. 18). The cartridge upper half 130 and the lower half 140 of the pair of puck anastomosis staplers 120 are moved back up the intestinal track to the gastric trocar seal 160 using magnetic laparoscopic positioner 150 and removed. An alternative embodiment would be to have a filament tether attached to the cartridge upper half 130 and the lower half 140 when inserted. Removal would merely require the gastric trocar iris be opened and the filament pulled to quickly remove the halves. Another alternative embodiment would be to only remove the anvil parts and leave the cartridge upper half 130 and the lower half 140 in the bowel 10 since after being fired they are merely crushed donuts of plastic and would normally pass through the GI tract. Using a laparoscopic linear cutter the jejunal loop 180 is transected and sealed at 182. The transected jejunal loop 180 is then removed from the abdomen through the gastric trocar seal 160.

An alternative device to anastomose a bowel is to use a circular stapler with a flexible shaft such as one manufactured by Power Medical, Inc. An exemplary embodiment utilizes this type of stapler by inserting circular staple heads into the intestinal tract by placing them into the mouth and down the esophagus. Accordingly a surgeon can then follow by placing the staples into the intestines transorally and utilizing the heads to anastomose portions of the intestines. It is also helpful to mark each anvil with a colored tag, or to have a colored filament or string proceeding from the anvil to the mouth so that the surgeon can identify a particular anvil of a number of anvils placed within the intestinal tract. A non-limiting disclosure of a surgical procedure utilizing the flexible-shaft circular staples can be found in U.S. Pat. No. 6,543,456 to Freeman, and is hereby incorporated by reference in its entirety. Using a laparoscopic linear cutter the jejunal loop 180 is transected and sealed 182. The transected jejunal loop 180 is then removed from the abdomen through the gastric trocar seal 160.

Figure 19:
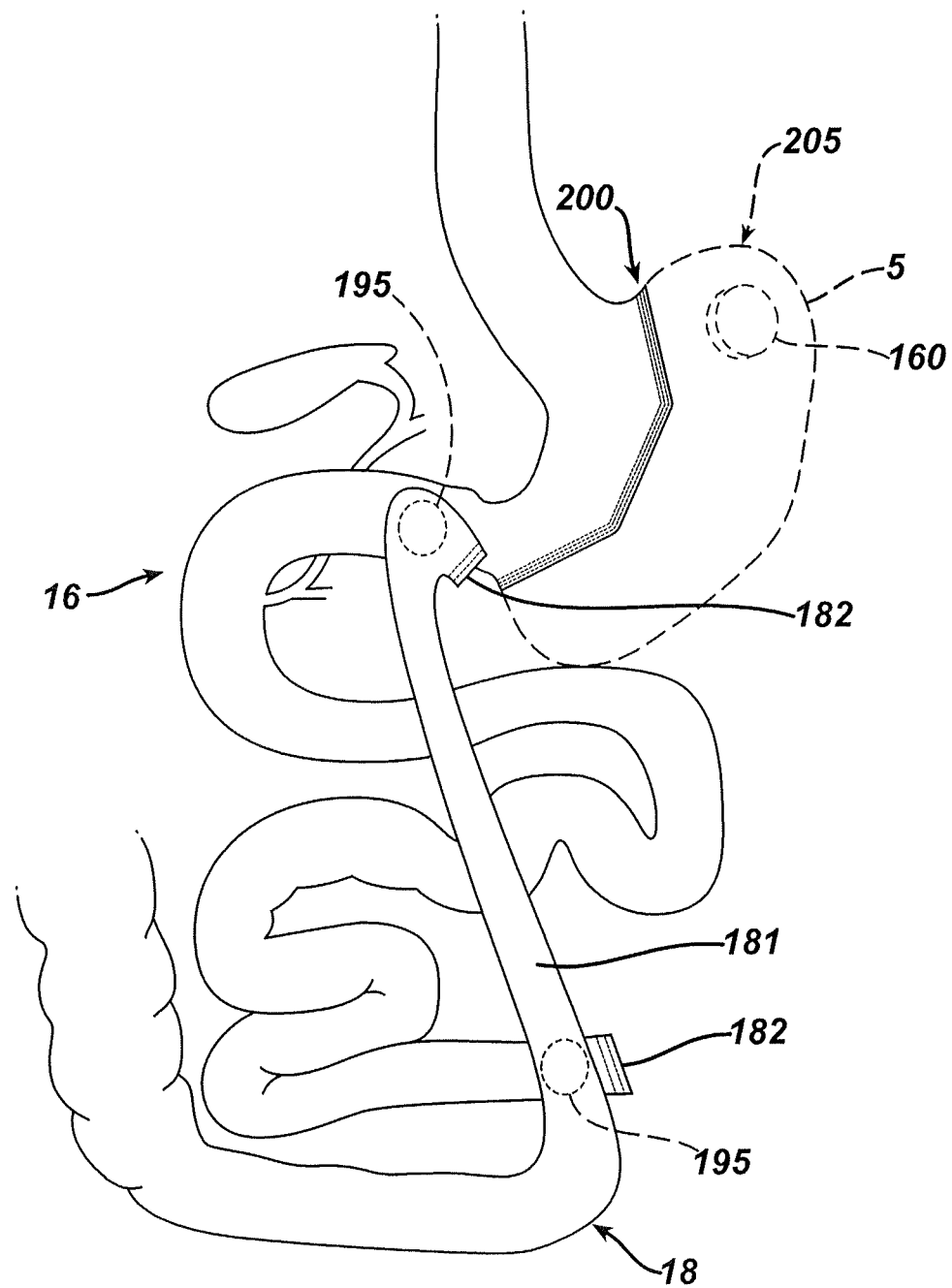
FIG. 19 is a schematic view of a gastrointestinal tract where a gastric sleeve has been created and circular anastomoses connect the ileum and jejunum via jejunum leg.

Turning to FIG. 19, a schematic view of a gastrointestinal tract where a gastric sleeve 200 has been created and circular anastomoses 195 connect the ileum 16 and jejunum 18 via jejunual leg 181. As previously described with reference to FIGS. 17 and 18, the laparoscopic linear cutter used to transect the jejunal loop 180 is then used to create a gastric sleeve 200 and a stomach specimen 205. Once separated, the gastric trocar seal 160 is removed from the stomach specimen 205 and both are removed through the opened head of the single port abdomen trocar.

Figure 20:
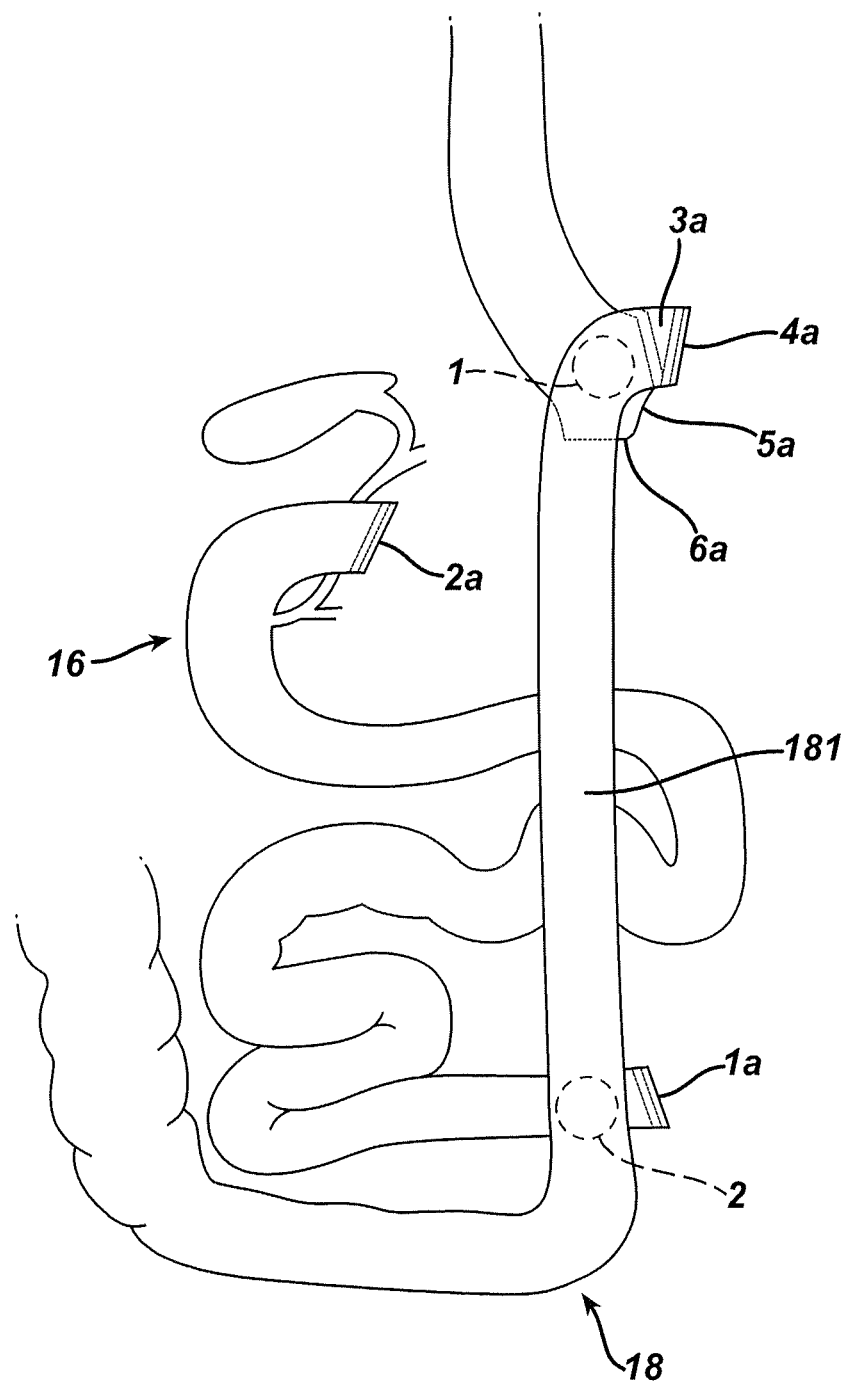
FIG. 20 is a schematic view of a hybrid bypass variant using the methods and devices of the present invention.

FIG. 20 is a schematic view of a hybrid bypass variant using the methods and devices of the present invention. As previously described with reference to FIGS. 16-18, application of the circular anastomoses procedure as disclosed forms anastomoses 1 and 2. As previously described with reference to FIGS. 17 and 18, the laparoscopic linear cutter is used to transect the jejunal loop 180 and the transections are sealed at 1a and 4a. Similarly the laparoscopic linear cutter is used to remove the stomach by cutting and sealing at 2a-3a and 5a-6a. The transected jejunal loop 180 is then removed from the abdomen through the opened head of the single port abdomen trocar as previously described.

Figure 21:
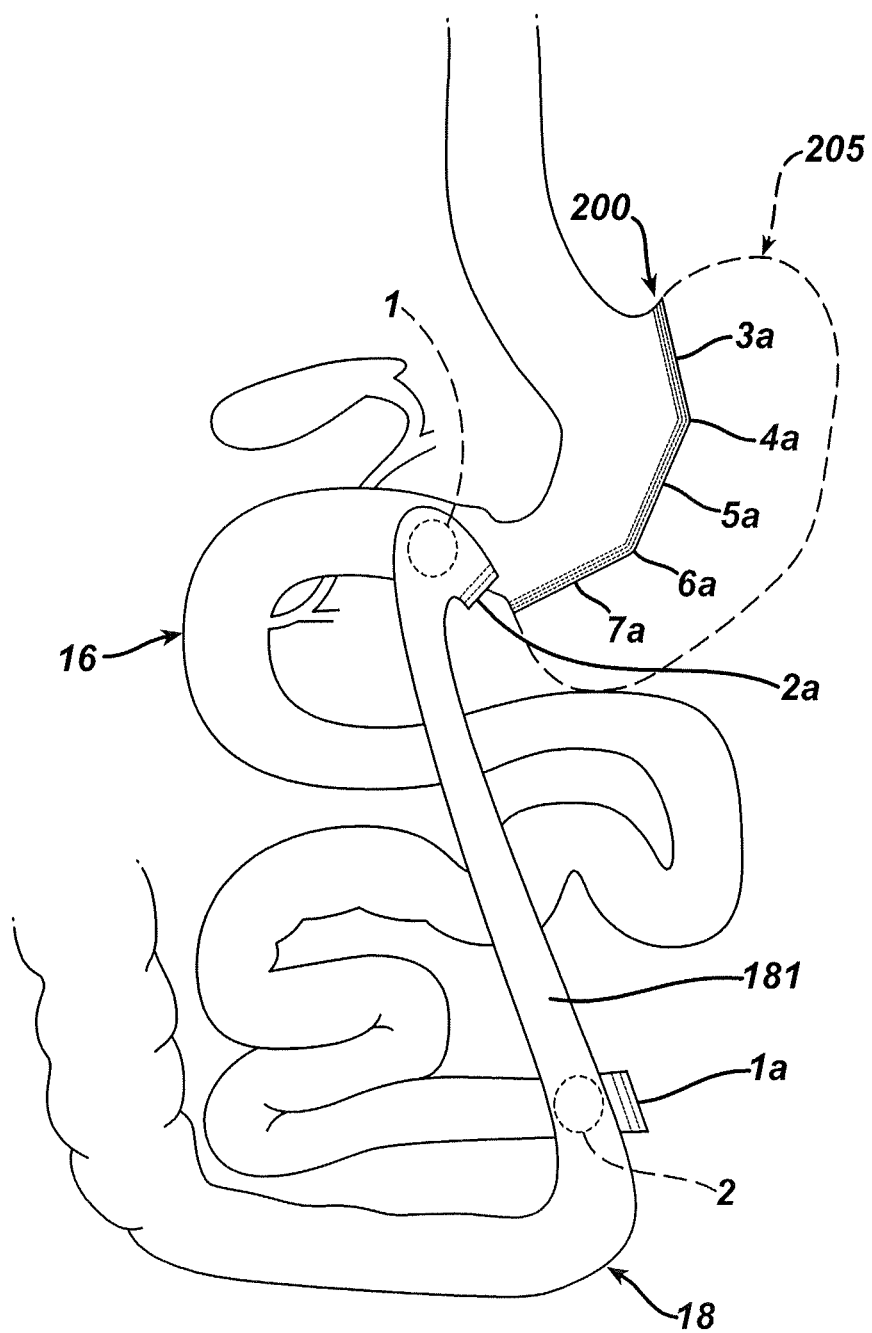
FIG. 21 is a schematic view of a hybrid "Y" variant without malabsorption.

FIG. 21 is a schematic view of a hybrid Y variant without malabsorption where a gastric sleeve 200 has been created and circular anastomoses 1 and 2 connect the ileum 16 and jejunum 18 via jejunum leg 181 using the methods and devices of the present invention. As previously described with reference to FIGS. 16-18, application of the circular anastomoses procedure as disclosed forms anastomoses 1 and 2. As previously described with reference to FIGS. 17 and 18, the laparoscopic linear cutter used to transect the jejunal loop 180 and the transections are sealed at 1a and 2a. The laparoscopic linear cutter is then used to create a gastric sleeve 200 and a stomach specimen 205 by cutting and sealing at 3a-7a. Once separated, the gastric trocar is removed from the stomach specimen 205 and both are removed from the abdomen through the opened head of the single port abdomen trocar as previously described.

Figure 22:
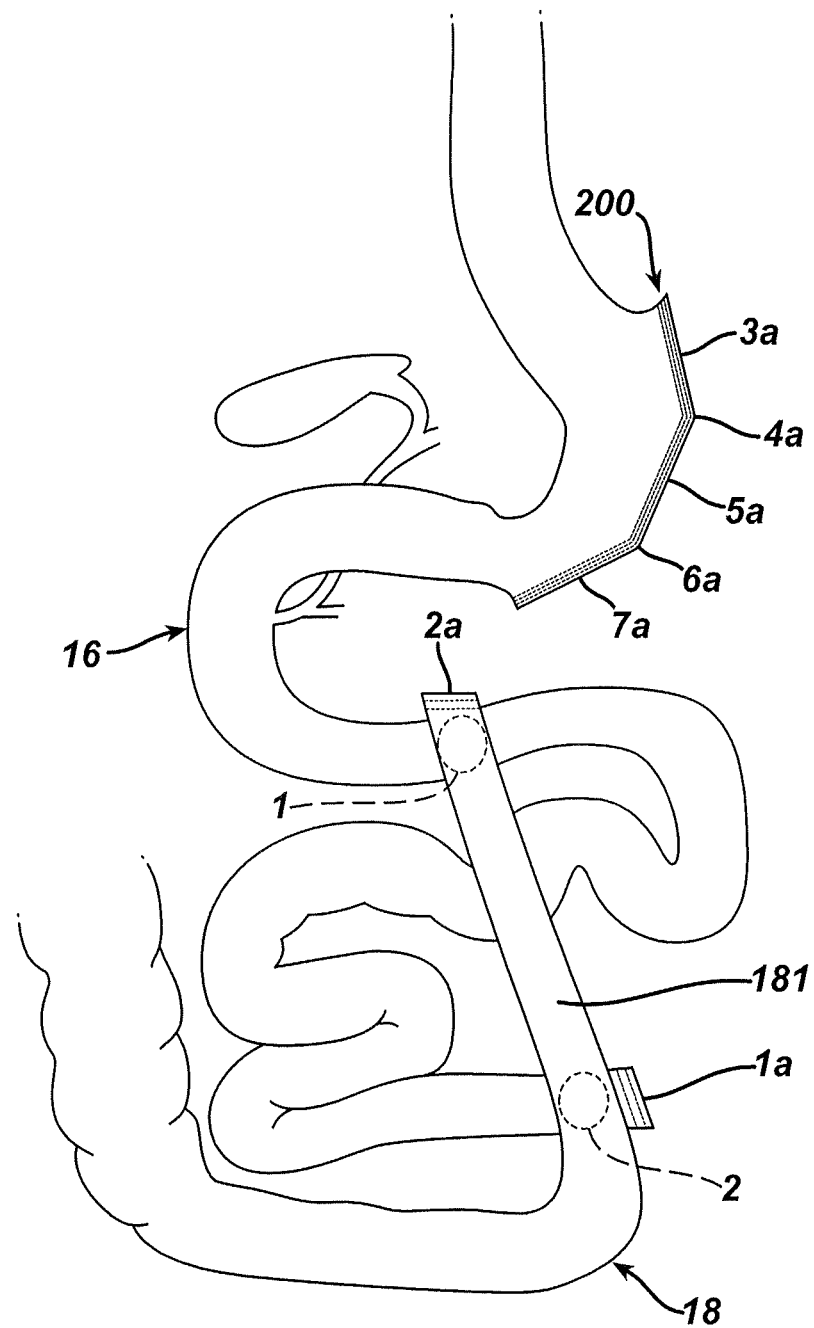
FIG. 22 is a schematic view of a hybrid "Y" variant with some malabsorption.

FIG. 22 is a schematic view of a hybrid Y variant with some malabsorption where a gastric sleeve 200 has been created and circular anastomoses 1 and 2 connect the lower ileum 16 and jejunum 18 via jejunum leg 181 using the methods and devices of the present invention. As previously described with reference to FIGS. 16-18, application of the circular anastomoses procedure as disclosed forms anastomoses 1 and 2. As previously described with reference to FIGS. 17 and 18, the laparoscopic linear cutter used to transect the jejunal loop 180 and the transections are sealed at 1a and 2a. The laparoscopic linear cutter is then used to create a gastric sleeve 200 and a stomach specimen (of the type shown in FIG. 21) by cutting and sealing at 3a-7a. Once separated, the gastric trocar is removed from the stomach specimen 205 and both are removed from the abdomen through the opened head of the single port abdomen trocar as previously described.

Figure 23:
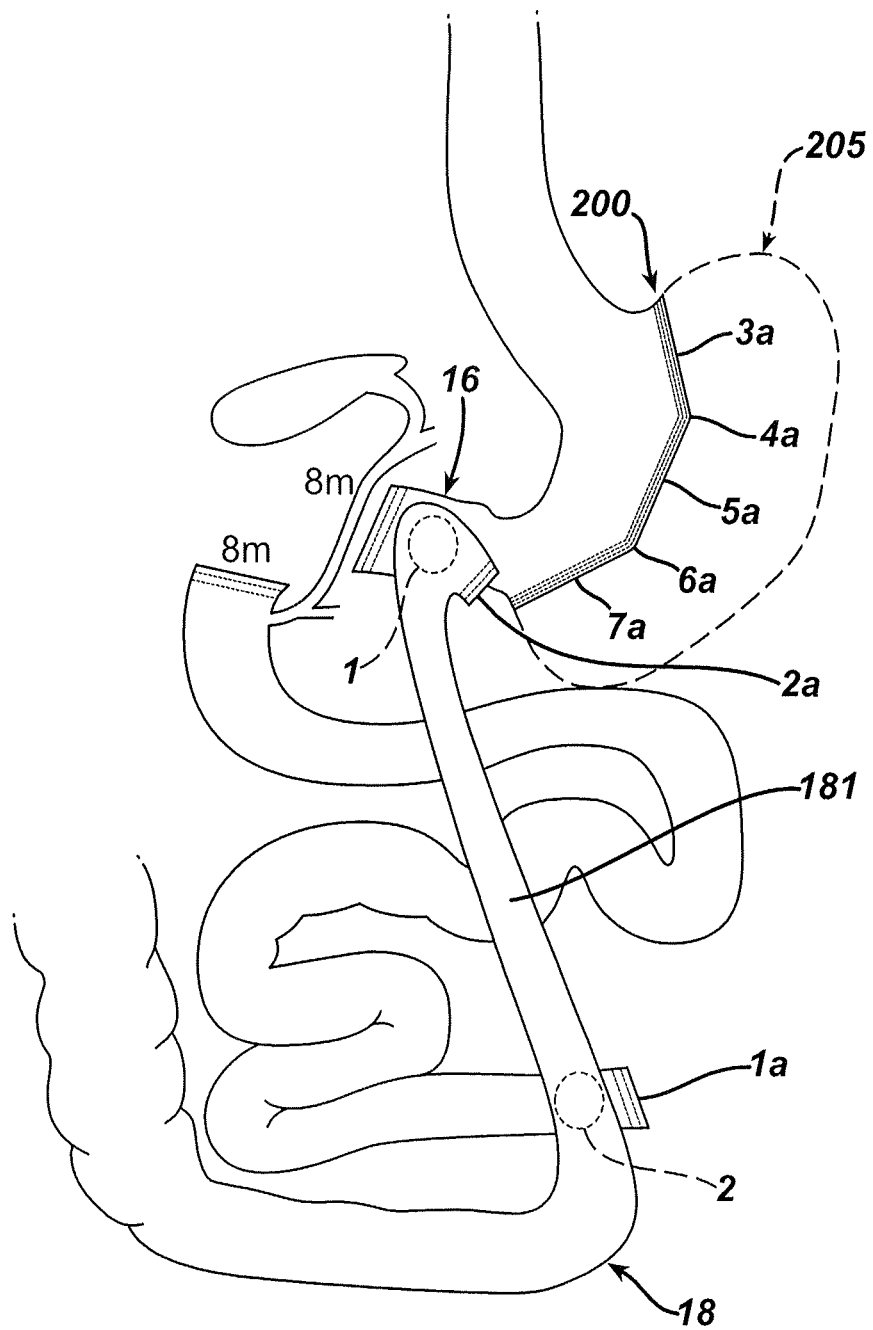
FIG. 23 is a schematic view of an intact pyloric sphincter bypass hybrid where a gastric sleeve has been created and circular anastomoses and 2 connect the ileum proximal the pyloric sphincter.

FIG. 23 is a schematic view of an intact Pyloric sphincter bypass hybrid where a gastric sleeve 200 has been created and circular anastomoses 1 and 2 connect the ileum 16 proximal the pyloric sphincter and jejunum 18 via jejunum leg 181 using the methods and devices of the present invention. As previously described with reference to FIGS. 16-18, application of the circular anastomoses procedure as disclosed forms anastomoses 1 and 2. As previously described with reference to FIGS. 17 and 18, the laparoscopic linear cutter used to transect the jejunal loop 180 and the transections are sealed at 1a and 2a. The laparoscopic linear cutter is then used to create a gastric sleeve 200 and a stomach specimen 205 by cutting and sealing at 3a-7a. In addition ileum 16 proximal the pyloric sphincter is cut and sealed at 8 m. Once separated, the gastric trocar is removed from the stomach specimen 205 and both are removed from the abdomen through the opened head of the single port abdomen trocar as previously described.

In order to prevent a stricture in the lumen at the site of the compression anastomoses 195, an absorbable stent or non-absorbable stent may be subsequently placed in the lumen at the site of the newly created anastomosis. A non-limiting disclosure of an absorbable stent can be found in U.S. Pat. No. 7,452,363 to Ortiz, which is hereby incorporated by reference in its entirety. A non-limiting disclosure of a non-absorbable stent can be found in U.S. Pat. No. 7,115,136, to Park et al., which is hereby incorporated by reference in its entirety. A non-limiting disclosure of an applier can be found in U.S. Pat. No. 7,309,341 to Ortiz et al., which is hereby incorporated by reference in its entirety.

Figure 24:
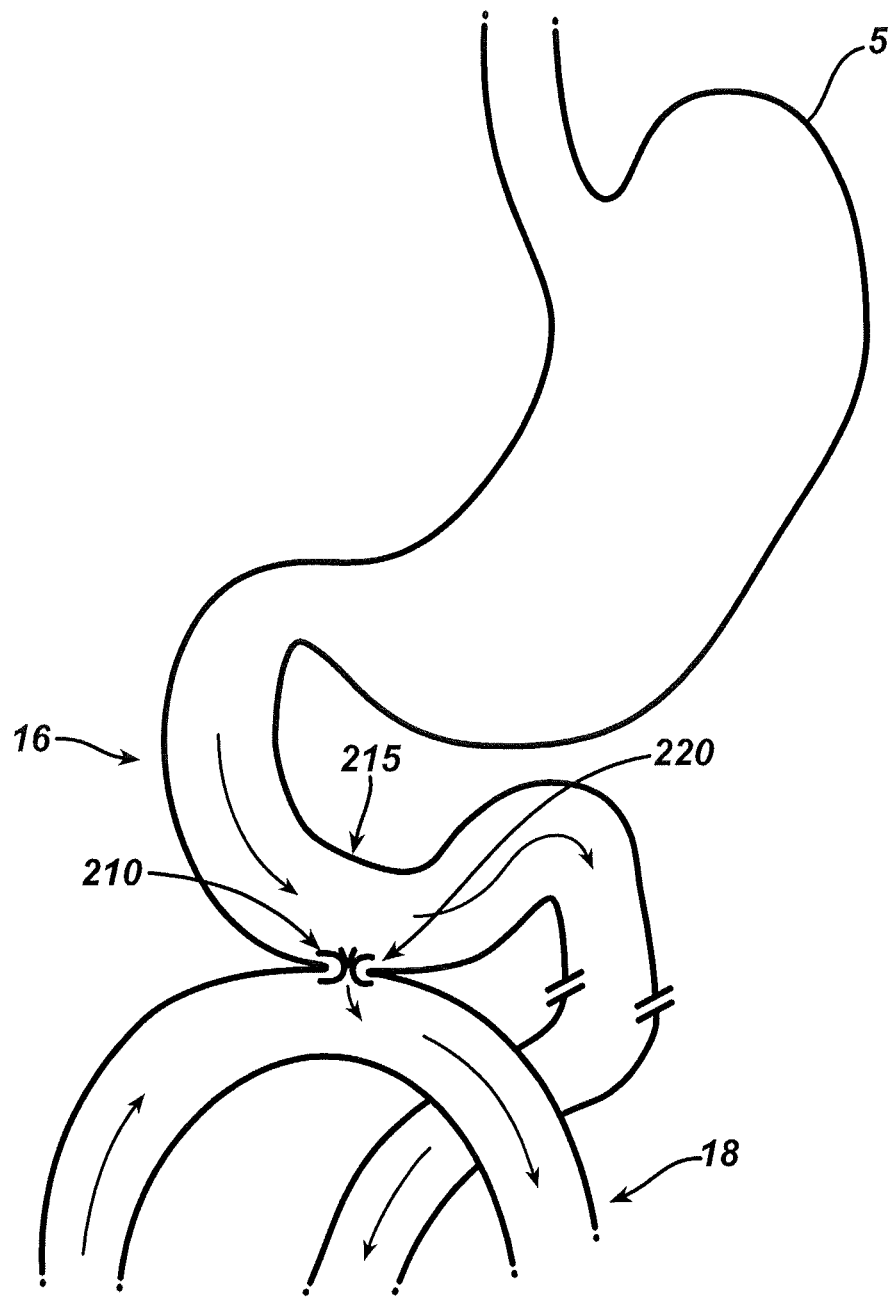
FIG. 24 is a schematic view of a gastrointestinal tract having a valve implant device.

FIG. 24 shows a schematic view of a gastrointestinal tract having a valve implant device 210 positioned at a proximal position 220. Chyme flow is indicated by arrows. The valve implant device 210 is an implantable device for bridging or linking the proximal portion of the gastrointestinal tract to the ileum and provides a solution for one-way redirection of nutrients directly to the ileum. Preferably, the proximal position 220 is at the stomach 5, duodenum 16 or proximal jejunum 215. The location may be based on patient needs such as body mass index (BMI) or selection based on an appropriate delay of the onset of satiety from start of a meal. The portion of the duodenum 16 just past the ampulla of vater may be preferred over the stomach 5 for pH compatibility reasons. Similarly, the proximal jejunum 215 may be preferred over both the stomach 5 and the duodenum 16 because of available length to reach the ileum whose distal end is constrained by the attachment of the colon to the abdominal cavity. Bridge locations may have other placements with the primary function remaining to: (a) provide nutrients which are present in the proximal intestinal tract to the ileum to trigger the ileal brake and (b) to provide these nutrients to the ileum soon after eating, i.e. earlier than would be expected during the course of a meal to activate physiologic processes related to satiety.

Figure 25A:
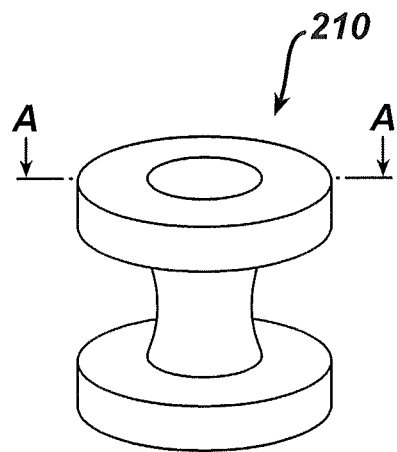
FIGS. 25a and 25b are a schematic view of the valve implant device and a schematic cross sectional view of the valve implant device.
Figure 25B:
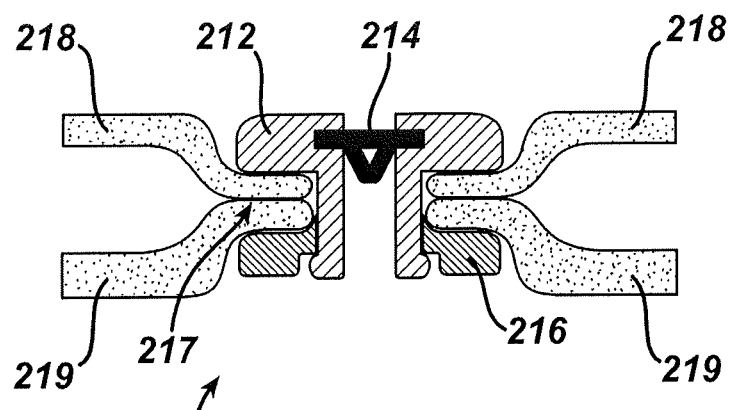

FIGS. 25a and 25b show a schematic view of the valve implant device 210 and a schematic cross sectional view of the valve implant device 210. In this embodiment, the valve implant device 210 uses a male and female connection to snap together and clamp into the lumen. The valve implant device 210 includes a male valve housing 212 and a one way valve 214 disposed adjacent the male valve housing 212. A female valve housing 216 couples with the male valve housing 212. The male valve housing 212 and the female valve housing 216 cooperate to compress a first tissue wall 218 and a second tissue wall 219 and form a tissue compression zone 217. The valve implant device 210 may incorporate a filter cover over the proximal inlet to the bridge conduit to prevent occlusion with food-stuff. In an alternative embodiment, the valve implant device 210 may be an absorbable or non-absorbable style stent, which would allow insertion in a small diameter and deployment to a large engagement diameter.

Figure 27A:
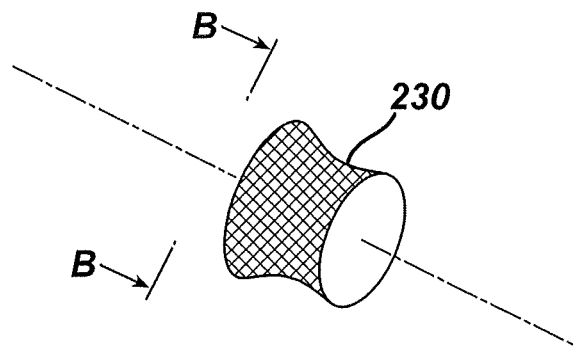
FIGS. 27a and 27b are a schematic view of the shunt device and a schematic cross sectional view of the shunt device.
Figure 27B:
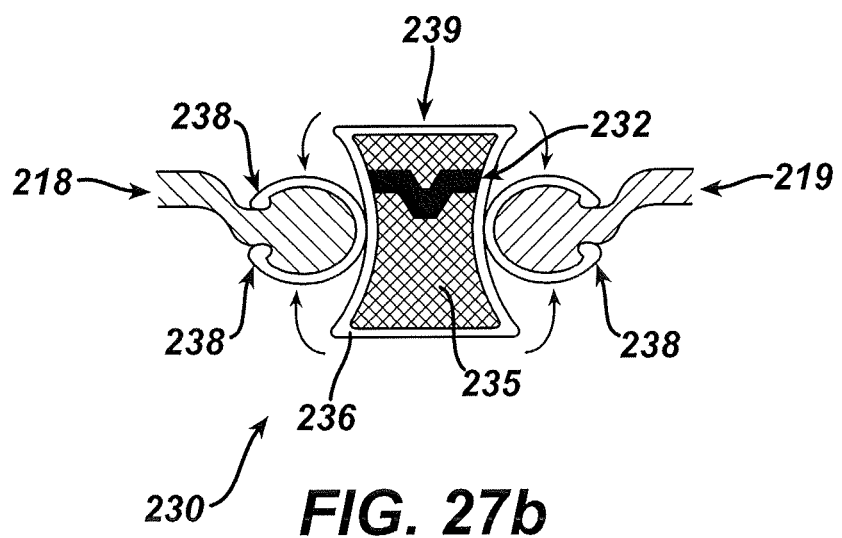

The valve implant device 210 may include a liner 235, as shown in FIGS. 27a and 27b, made of synthetic materials including: polyurethane, ePTFE, polyethylene terphthalane, or similar. One suitable high molecular weight polyethylene is sold under the brand name Spectra. A suitable PET material is commercially available under the brand name Dacron. Alternatively, liner 235 can be formed from a sheet of material which is either itself impervious to blood flow, or covered with a coating which renders the material impervious. In still other embodiments liner 235 is a film, sheet or tube of biocompatible material such as ePTFE. Further, the valve implant device 210 may be formed or made entirely or in part from biological materials such as pericardial tissue. There is a wide range of biologically based valves made of natural valves or composed of biological materials such as pericardial tissue. Furthermore, in accordance with another preferred embodiment of the present invention, the valve implant device 210 is provided with radio-opaque material, so as to help tracking the valve device operation in vivo. The valve implant device 210 may have alternate forms and placements within the GI tract without departing from the scope of the present invention.

Figure 26A:
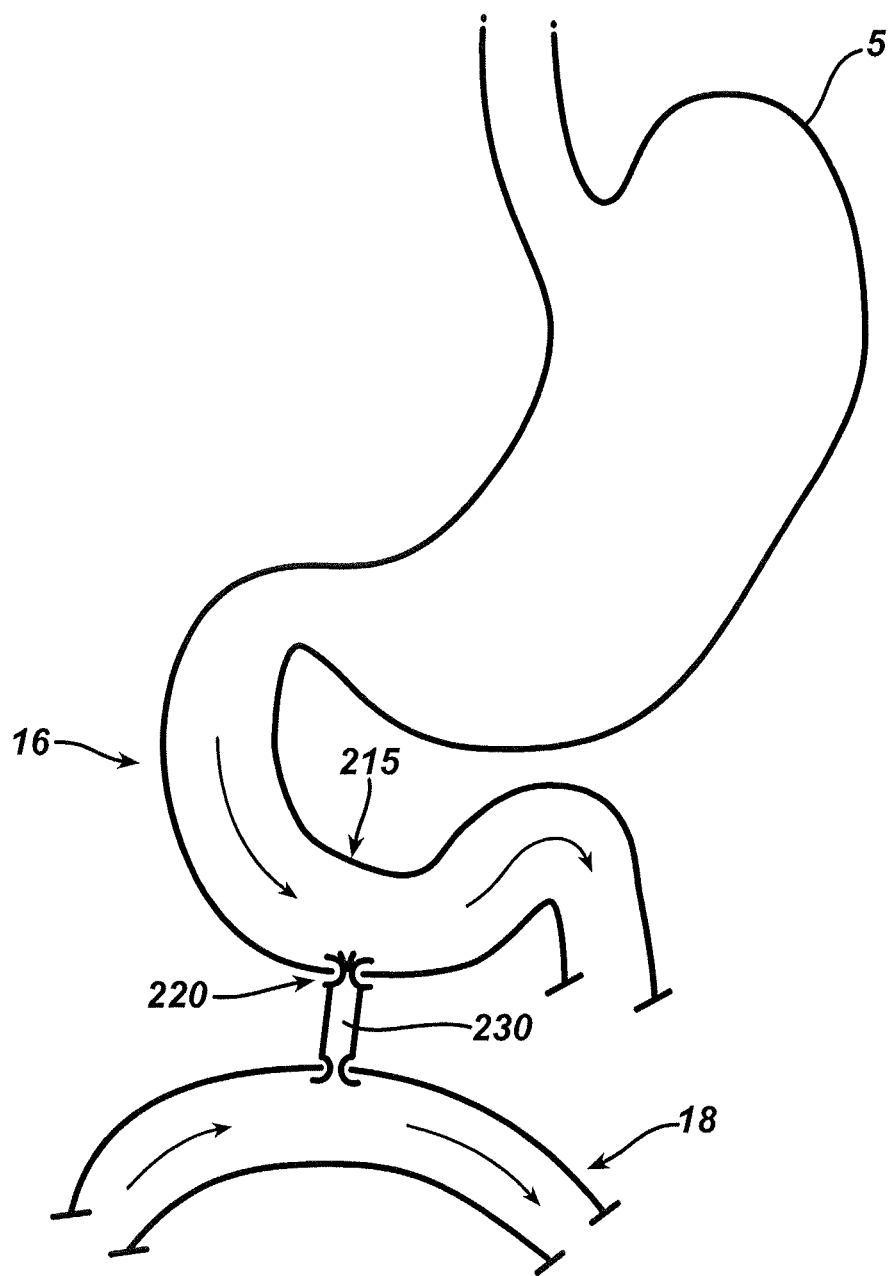
FIG. 26a is a schematic view of a gastrointestinal tract having a shunt device positioned at a proximal position.
Figure 26B:
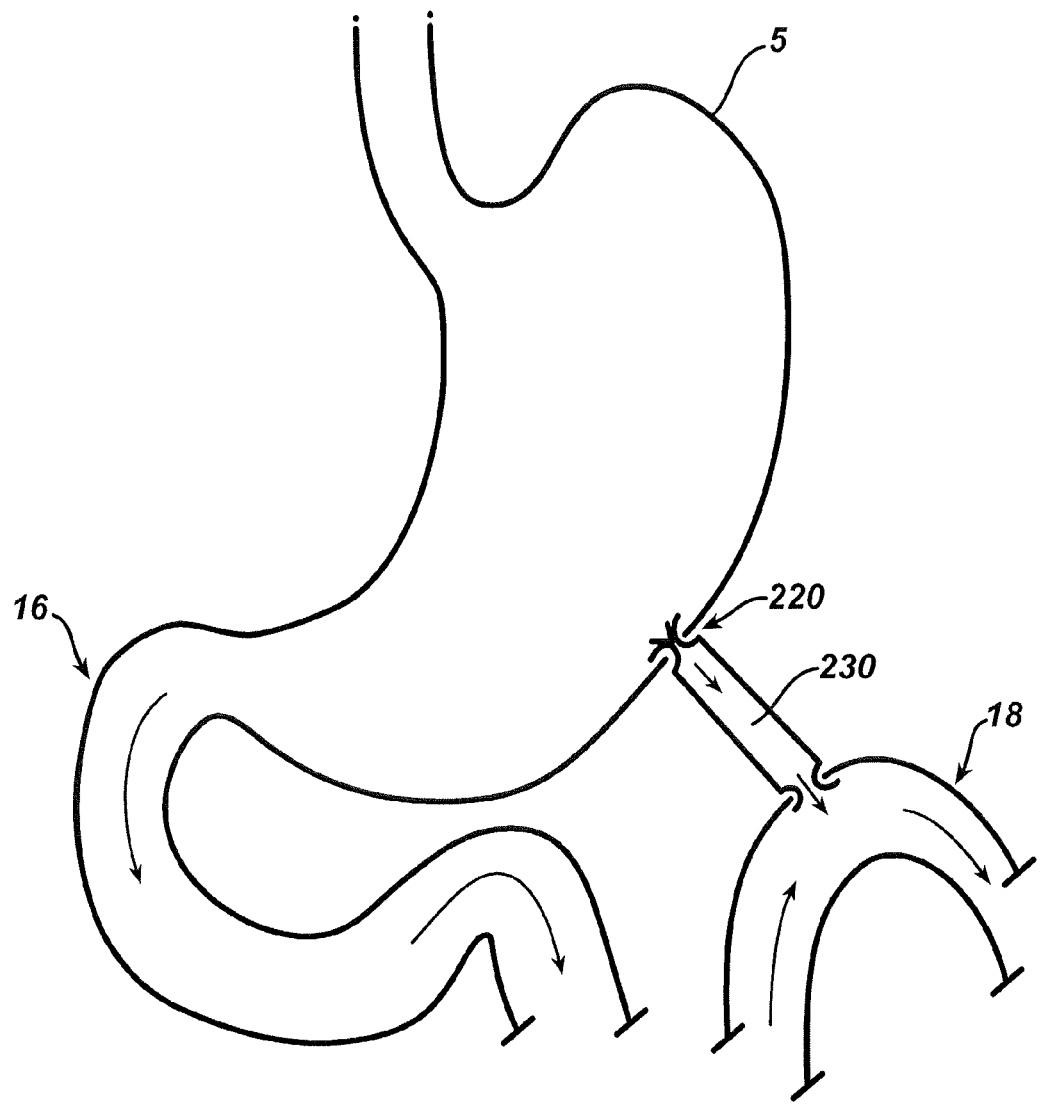
FIG. 26b is a schematic view of a gastrointestinal tract having a shunt device positioned at the stomach.

FIG. 26a shows a schematic view of a gastrointestinal tract having a shunt device 230 positioned at a proximal position 220. Chyme flow is indicated by arrows. In this embodiment, the shunt device 230 bridges or links the proximal portion of the gastrointestinal tract to the ileum. Preferably, the proximal position 220 is at the stomach 5, duodenum 16 or proximal jejunum 215. The shunt device 230 is shown placed with the proximal position 220 at the stomach 5 in FIG. 26b. As may be appreciated, location selection may be based on patient needs such as body mass index (BMI) or selection based on an appropriate delay of the onset of satiety from start of a meal. The portion of the duodenum 16 just past the ampulla of vater may be more preferred over the stomach 5 for pH compatibility reasons. Similarly, the proximal jejunum 215 may be preferred over both the stomach 5 and the duodenum 16 because of available length to reach the ileum whose distal end is constrained by the attachment of the colon to the abdominal cavity. Bridge locations may have other placements with the primary function remaining to: (a) provide nutrients which are present in the proximal intestinal tract to the ileum to trigger the ileal brake and (b) to provide these nutrients to the ileum soon after eating, i.e. earlier than would be expected during the course of a meal to activate physiologic processes related to satiety. Further, the inclusion of a one way valve provides a solution for one-way redirection of nutrients directly to the ileum. Details of such valves are disclosed herein with respect to FIGS. 43b and 43c.

FIG. 27a and shows a schematic view of the shunt device 230 and FIG. 27b shows a schematic cross sectional view of the shunt device 230. The shunt device 230 is a one-way valve implant device incorporating a conduit section which provides compression to tissue so as to facilitate the joining of these tissues via a lumen. The shunt device 230 includes walls 236 forming the conduit section are preferable formed of a pliable material. The walls 236 are of interwoven wire surrounding a liner 235. The interwoven wire is a flexible wire mesh which allows the shunt device 230 to fixture itself to the lumen. A woven shape memory version of such a device and an associated applier may be found in U.S. Pat. No. 7,115,136 and in U.S. Pat. No. 7,309,341, respectively. Alternatively, a non-shape memory alloy version of this device may be utilized, wherein the stent may yield under the application load and then sutured into place.

A one way valve 232 is disposed adjacent the liner 235. The shunt device 230 includes compression portions 238 for coupling the shunt device 230 to a first tissue wall 218 and a second tissue wall 219 as indicated by arrows. Preferably the shunt device 230 permits in-growth of adjacent tissue after placement. Further, the shunt device 230 includes a filter cover over the proximal inlet 239 to prevent occlusion with food-stuff. The shunt device 230 may be formed of synthetic materials including: polyurethane, ePTFE, polyethylene terphthalane, or similar materials. Similarly, the shunt device 230 may be formed entirely or in part from biological materials such as pericardial tissue.

Methods of the present invention allow a physician to treat obesity by selecting the delay of the onset of satiety from the start of meal with appropriate proximal placement of the valve implant device 210 or the shunt device 230. These devices can be utilized or placed laproscopically providing both short-term weight loss and sustained long-term excess weight loss. The devices herein may also be effective in treating type-2 diabetes. Further, the devices can be used alone or adjunctively and synergistically with current bariatric procedures such as gastric banding. It is to be appreciated that removing the bridge and adjacent tissue renders the procedure at least somewhat reversible.

FIGS. 28a-d show schematic views of ileal pouches formed on the proximal portion of the ileum 250. Creation of an ileum or juxtaposed chyme reservoir makes an available chyme source that can be used to provide chyme to the ileum and thereby induce intestinal brake when eating starts. The intent is to increase the time that the intestine holds chyme between eating. Once eating commences the chyme would move deeper into the ileum to have the L-cells secrete GLP-1 thus inducing intestinal brake. In a first embodiment, rerouting chyme involves creating the ileal pouch to contain the chyme reservoir by connecting folds of the ileum 250. In this embodiment the ileum remains together with input from jejunum and emptying through the cecum. Various pouch configurations are contemplated such as a J-pouch 241 as in FIG. 28a which has a pouch length of between fifteen to twenty centimeters, a lateral pouch 242 as in FIG. 28b having a pouch length of between ten to twelve centimeters, an S-pouch 243 as in FIG. 28c having a pouch length between twelve to fifteen centimeters and a W-pouch 244 as in FIG. 28d having a pouch length between twelve to fifteen centimeters. However, as, the pouch may be of any suitable configuration or dimension and it should be understood that the aforementioned pouch configurations and dimensions are non-limiting examples and other configurations are contemplated without changing or altering the scope of the present invention.

Figure 28A:
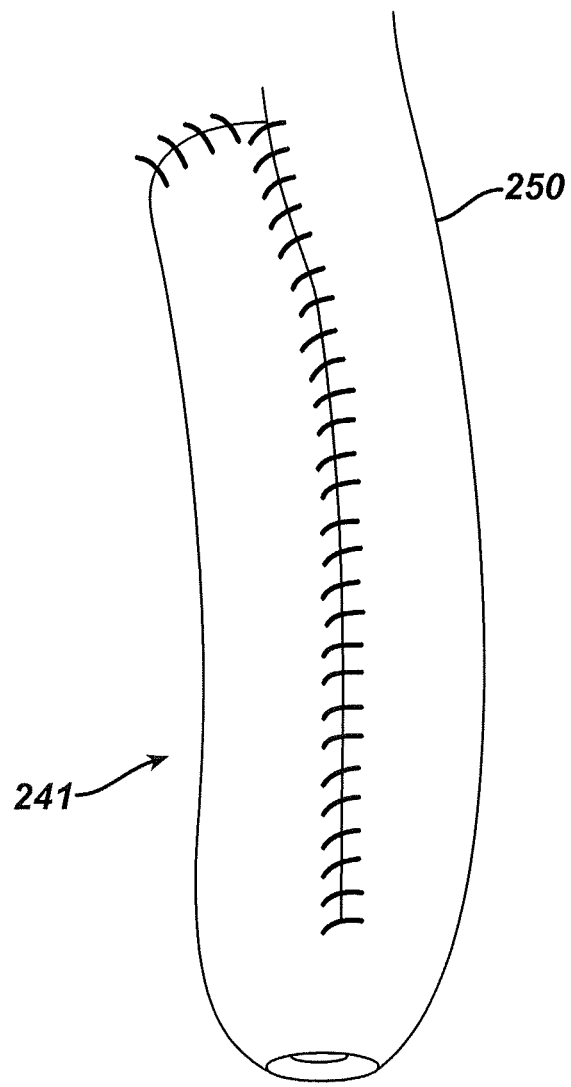
FIGS. 28a-d are schematic views of ileal pouches formed on the proximal portion of the ileum.
Figure 28B:
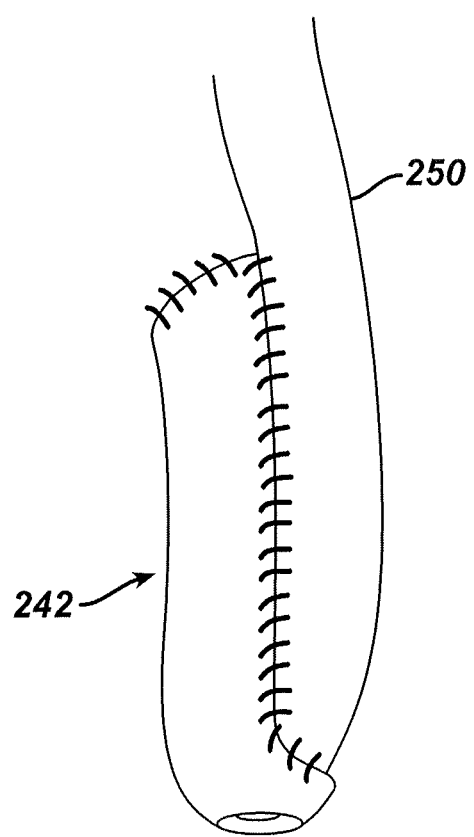
Figure 28C:
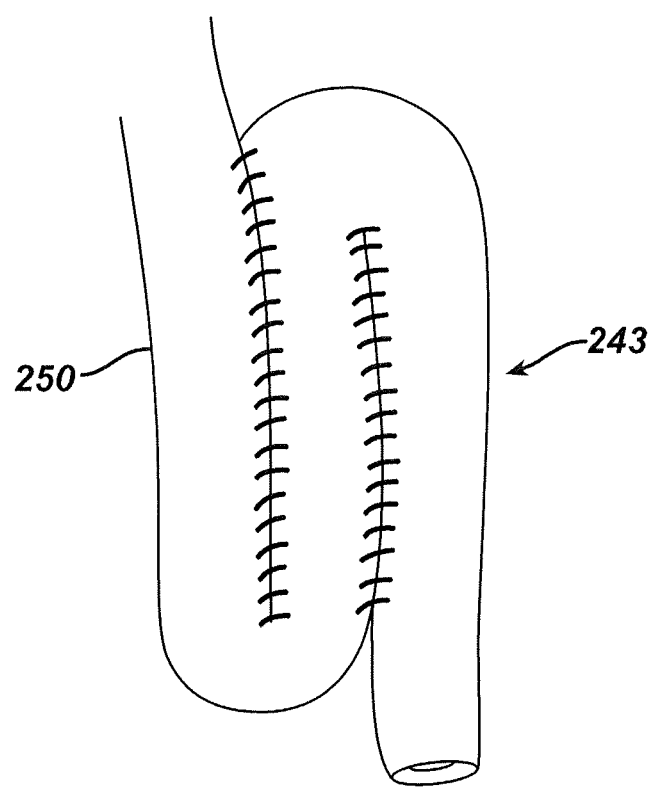
Figure 28D:
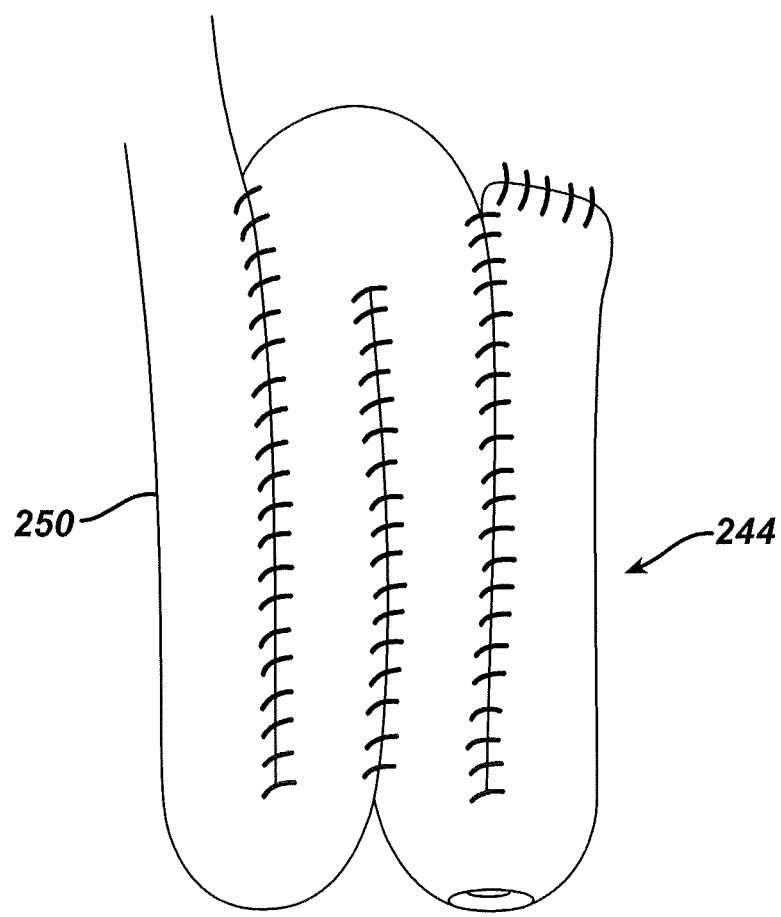

In the pouch procedure, a stoma is created in a section of the ileum to form an anastomosis to the remaining rectal stump. Such pouches could be created by firing an Endocutter intralumenally across adjoining layers of intestinal wall. In a preferred embodiment, an endocutter is inserted into the bowel through an enterotomy and the intestine segmented. After the intestinal segment is anastomosed, the enterotomy may be closed by another firing of a linear cutter across the enterotomy or may be closed by use of a suture. Similar pouches could be created in the duodenum or jejunum due to the presence of L-cells and other cells that may trigger satiation signals. It is further contemplated that satiating signals involve endocannabinoid receptors. As shown in FIG. 28d, the pouch can be made up of several side to side anastomoses while leaving the lumens mainly disconnected from each other. The chyme would still move through using peristalsis action without getting hung up in a giant pouch. The benefit is that the chyme is allowed to proceed quickly through the GI tract through the side holes. As may be appreciated, pouch placement could be done anywhere along the GI tract which results in effectively shortening the traverse of the bowel without departing from the scope of the present invention. The complete or partial evacuation of the reservoir may be accelerated by stimulating the muscle walls of the ileum/jejunum or activating a pump action along the bowel.

Figure 29A:
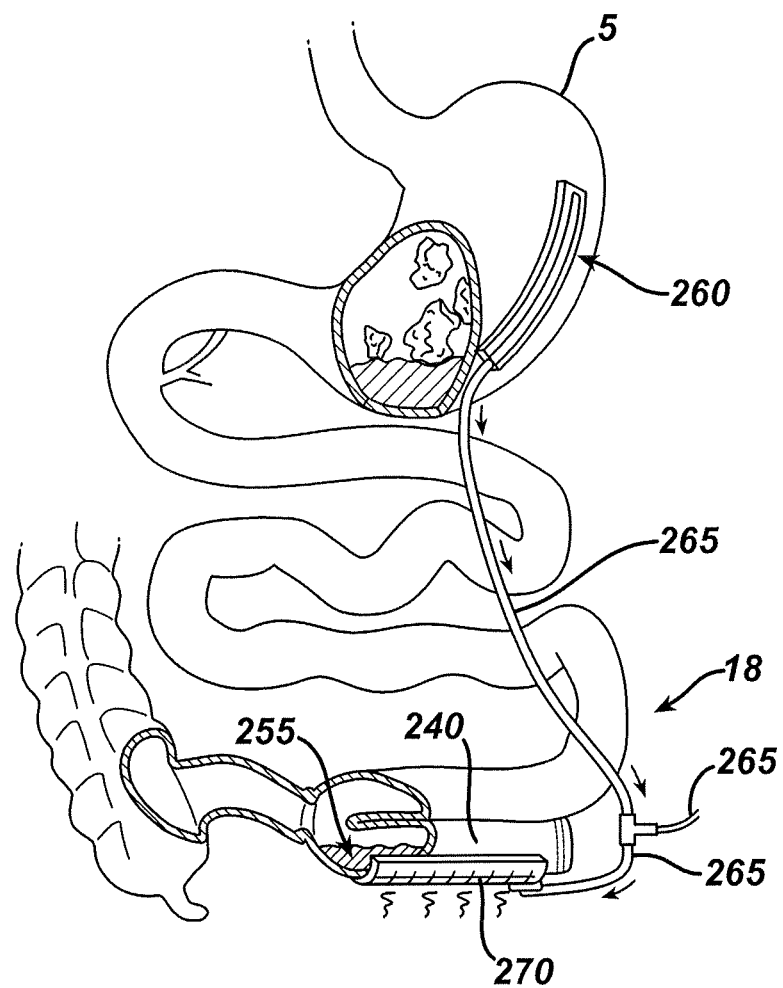
FIG. 29a is a cut away view of an ileal pouch containing a chyme reservoir formed via an ileal pouch on a portion of the ileum.

FIG. 29a shows a cut away view of a chyme reservoir 255 formed via an ileal pouch 240 on a portion of the ileum 18. In this particular embodiment, fat or glucose reaching the ileum 18 contributes to L-cell stimulation and production of the GLP-1 hormone that signals satiety. Creation of the ileum or juxtaposed chyme reservoir 255 makes available a source of fat or glucose that is used to trigger production of the GLP-1 hormone when eating starts. In a first embodiment, rerouting chyme involves creating the ileal pouch 240 to contain the chyme reservoir 255 by connecting folds of the ileum 18. Various pouch configurations are contemplated such as described with reference to FIGS. 28a-d. As shown in FIG. 29a, the ileal pouch 240 is created by performing a side to side anastomosis of a portion of the ileum, or in a preferred embodiment, a transplanted portion of another segment of bowel to this location. This anastomosis may be performed by a firing of a linear cutter without a knife. Subsequently, the enterotomy used to perform the side to side anastomosis is closed by another firing of a linear cutter or may be closed by sutures.

Still referring to FIG. 29a, a sensor 260 in communication with the stomach 5 detects the pH of the stomach. The sensor 260 uses a change in pH to identify when the stomach 5 is being filled. Alternatively, it is contemplated that the sensor 260 is in communication with the proximal duodenum and uses a change in pH to identify when the stomach 5 is being filled. A change in pH is normally associated with meal consumption or the commencement of eating or anticipation of eating.

Figure 29B:
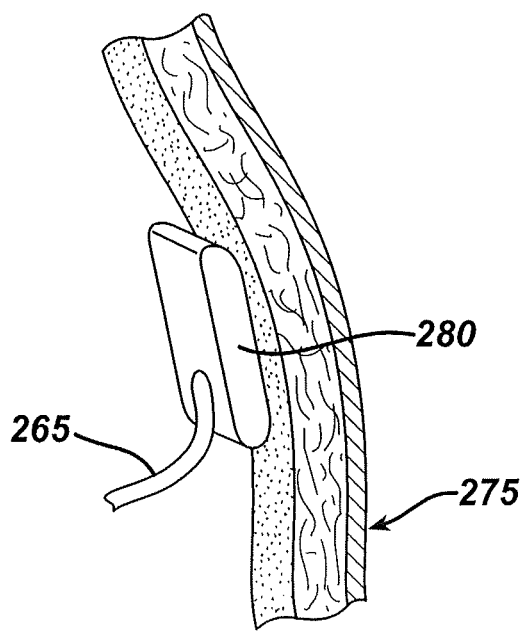
FIG. 29b is a cross sectional view of a power pack/transmitter coupled to an abdominal wall.

FIG. 29b shows a cross sectional view of a power pack/transmitter 280 coupled to an abdominal wall 275. Communications means 265 couples the power pack/transmitter 280 to sensor 260 and the means to activate peristaltic response 270. The sensor 260 detects the change in pH and generates an output signal which is communicated to the power pack/transmitter 280 via the communications means 265. The power pack/transmitter 280 initiates peristaltic response of the ileal pouch 240 and the chyme reservoir 255 by activating the means to activate peristaltic response 270 via communications means 265.

Figure 29C:
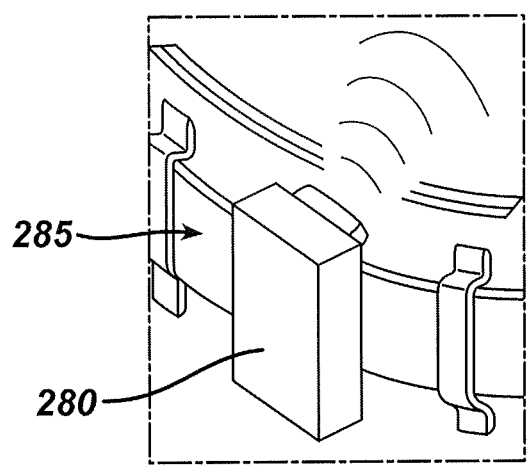
FIG. 29c is the power pack/transmitter worn externally on a belt.

In one embodiment the sensor 260 and means to activate peristaltic response 270 are in wireless communication with the power pack/transmitter 280 which is worn externally on a belt 285 as shown in FIG. 29c. The power pack/transmitter 280 may have alternate forms and placements, with the primary function remaining to signal the means to activate peristaltic response 270.

An exemplary embodiment contemplates the sensor 260 is an internal pH measuring device. The pH measuring device may be swallowable such as the iPill available from Phillips of Amsterdam, the Netherlands, or the SMARTpill available from the Smartpill Corporation of Buffalo, N.Y. In the preferred embodiment the internal pH measuring device is implanted in the stomach 5 rather than swallowed. In an alternate embodiment, the sensor 260 is implanted on the exterior of the stomach 5 with a sensing probe extending through the stomach wall into the stomach interior. A serosal to serosal tissue fold can be used to hold the sensor probe in place within the stomach. In an alternate embodiment, a pH sensor may be swallowed prior to a meal to act as a trigger for the chyme pouch.

Figure 30:
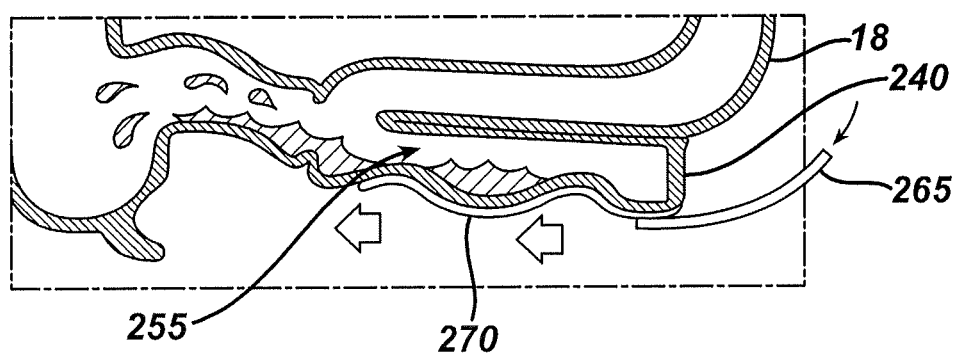
FIG. 30 is a schematic view of the chyme reservoir undergoing peristaltic response.

FIG. 30 is a schematic view of the chyme reservoir undergoing peristaltic response. The means to activate peristaltic response 270 activates peristaltic response at the ileal pouch 240, pushing the contents of the chyme reservoir 255 out of the ileal pouch 240 and leading to stimulation of the L-Cells to produce GLP-1 and a resulting satiation. The partial or complete evacuation of the chyme reservoir 255 may be accelerated by stimulating the muscle walls of the ileum/jejunum either concurrently or in sequence either before or after the means to activate peristaltic response 270 is activated. Further, two or more pouches may be used. The outlet flow of chyme from a first pouch could be controlled as needed such as, for example, by a valve. The valve may be controlled using embodiments as described herein.

Figure 31:
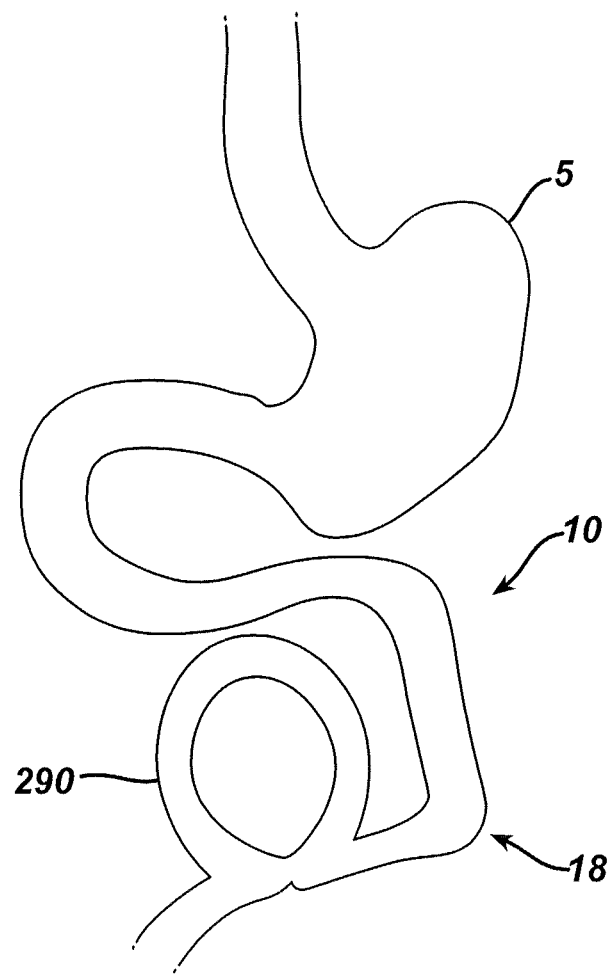
FIG. 31 is a schematic view of a gastrointestinal tract following the creation of a recirculation loop.

FIG. 31 shows a schematic view of a gastrointestinal tract following the creation of a recirculation loop 290. In this particular embodiment, looping the small bowel 10 recirculates digestive nutrients to induce the intestinal brake for increased satiety. Looping the small bowel 10 by moving the ileum 18 proximally with respect to its original position results in nutrients inducing the intestinal brake earlier and leads to quicker satiation. The rerouting of chyme exposes the ileum 18 to nutrients for a longer period of time and satiety is prolonged. The loop can be made using principles outlined in United States Patent Application Publication number US2006/0271075 to Bilotti et al, hereby incorporated herein by reference in its entirety.

Figure 32:
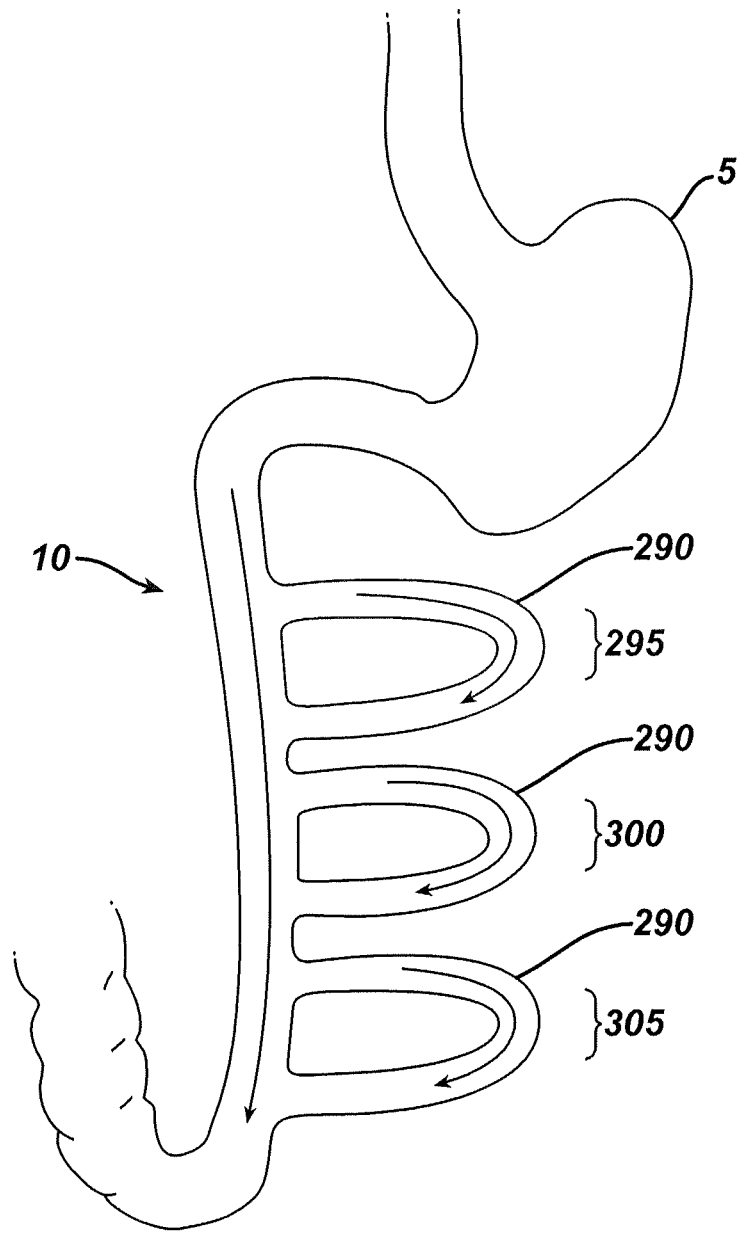
FIG. 32 is a schematic view of a gastrointestinal tract following the creation of more than one recirculation loop.

FIG. 32 shows a schematic view of a gastrointestinal tract following the creation of more than one recirculation loop 290. In this alternative embodiment, multiple recirculation loops 290 within the small bowel 10 are formed. The recirculation loop 290 is formed in the duodenal region 295, in the jejunal region 300 and in the ileal region 302 of the small bowel 10 as shown in FIG. 32. More than one recirculation loop 290 can be used and alternate placements are contemplated with the primary function remaining to recirculate digestive nutrients to induce the intestinal brake for increased satiety. In an alternative embodiment, a one way valve is provided in the recirculation loop 290 in order allow chyme to move distally in order to produce the ileal brake without the undesired flow of chyme in the proximal direction.

Figure 33:
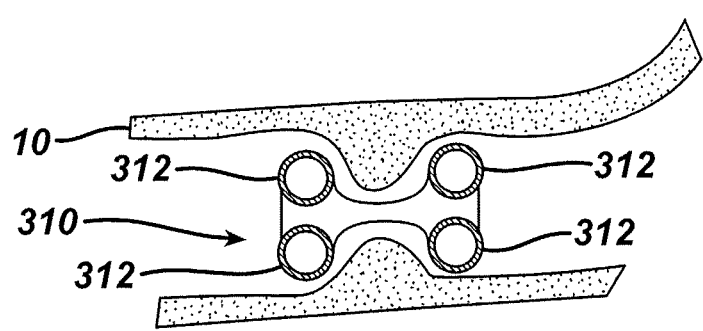
FIG. 33 is a schematic view of a section of bowel following the implantation of an inflatable shunt anchor.

FIG. 33 shows a schematic view of a section of bowel 10 following the implantation of an inflatable shunt anchor 310. The inflatable shunt anchor 310 uses inflatable portions 312 to fix the inflatable shunt anchor 310 to the walls of the bowel 10. In this embodiment it is contemplated that the inflatable shunt anchor 310 includes a one way valve. In an alternative embodiment, one such one-way valve may be a prosthetic flapper valve which is inserted endoscopically and stitched into place by an endoscopic stitching device or passing a needle endoscopically and using endoscopic graspers to stitch the device into place. In an alternate embodiment, an elastomeric, flexible duckbill valve may be implanted and similarly attached by suture or stapling. This valve could be compliant with the bowel, avoiding interference with peristalsis. Such a valve could also be placed endoscopically. In another alternative embodiment, an anatomical flapper valve made by folding lumen wall tissue in upon itself could be used. Further, the anatomical flapper valve is made biologically compatible by taking a harvested portion of intestine or blood vessel and intussuscepting the vessel such that a flapper valve is created. An anastomosis joins the ends of the biologically compatible anatomical flapper valve to the target portions of lumen ensures biocompatibility, particularly if the tissue is autologous tissue. Suture or t-tags could be used to hold the tissue in place until the serosa to serosa contact surface could heal together.

Figure 34:
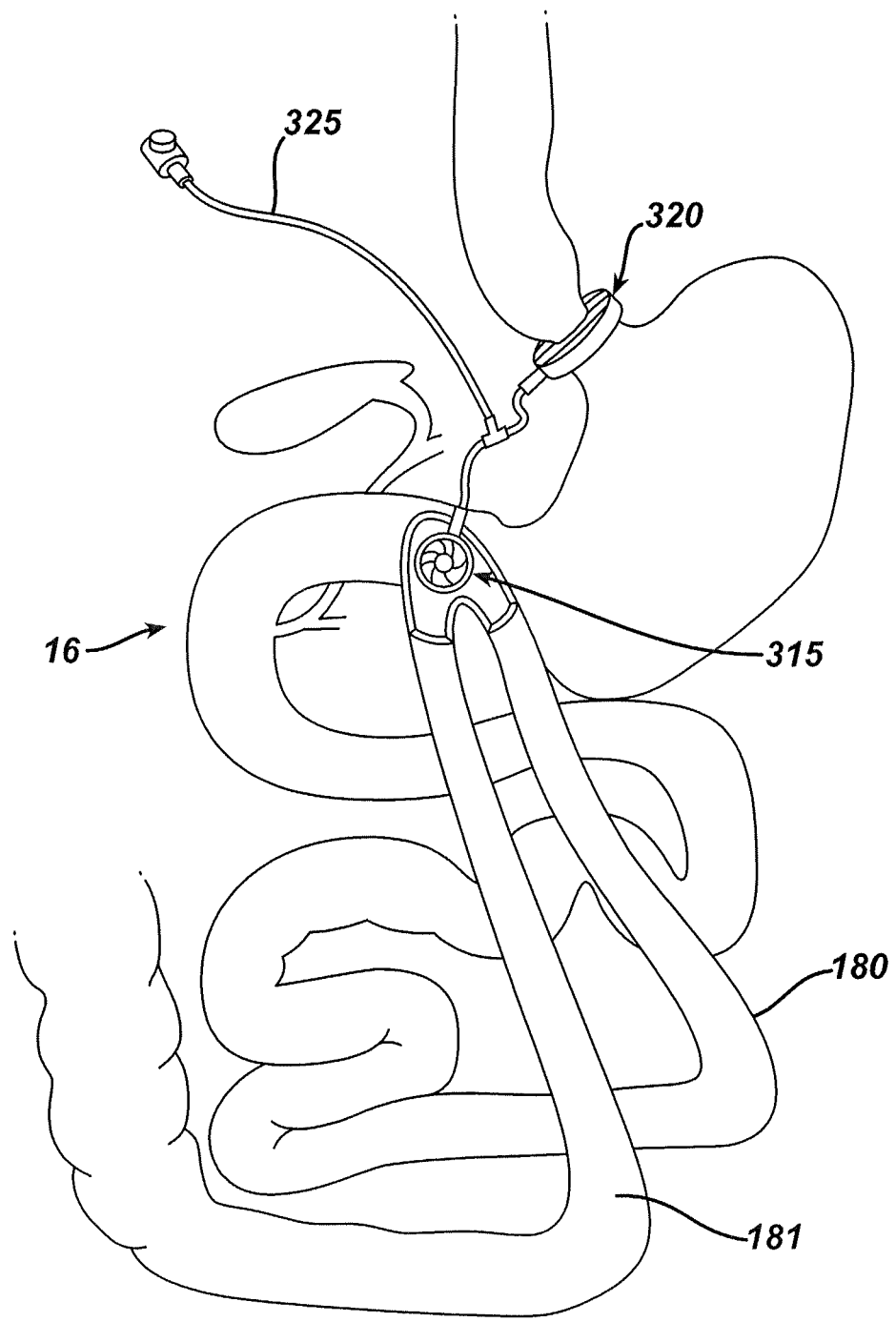
FIG. 34 is a schematic view of a gastrointestinal tract following the performance of the hybrid band procedure.

FIG. 34 is a schematic view of a gastrointestinal tract following the performance of a hybrid band procedure. The hybrid band procedure implants a valve 315 in the location of a single anastomosis between the proximal duodenum and the ileum. In a preferred embodiment, the valve 315 is implanted in conjunction with the performance of the jejunum loop as described with reference to FIGS. 16-23. The hybrid band procedure is a reversible metabolic impacting procedure as reversal requires only removal of the valve 315 and closure of both otomies. Further, the valve 315 could be tied to a tethered gastric band 320 via a communications means 325 and used in conjunction with the tethered gastric band 320 to improve the effects of a gastric band intervention which will be described. After the patient starts eating the stomach begins to expand and contract and pressure is exerted on the tethered gastric band 320. The tethered gastric band 320 senses this pressure and applies pressure to the valve 315 is via communications means 325. The valve 315 remains open for a predetermined duration as described then the pressure is bled off and the valve 315 closes leaving the remainder of the digestive process unchanged.

Figure 35A:
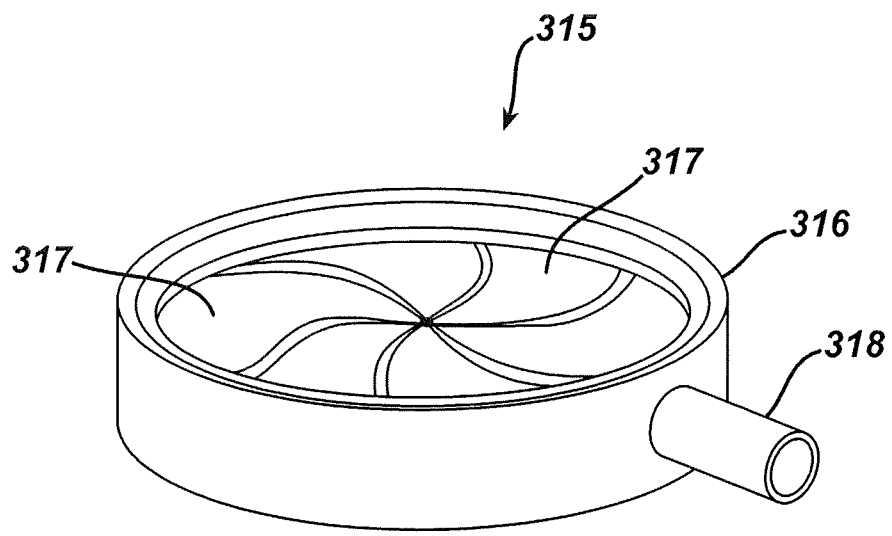
FIG. 35a is a view of the valve of the hybrid band procedure.
Figure 35B:
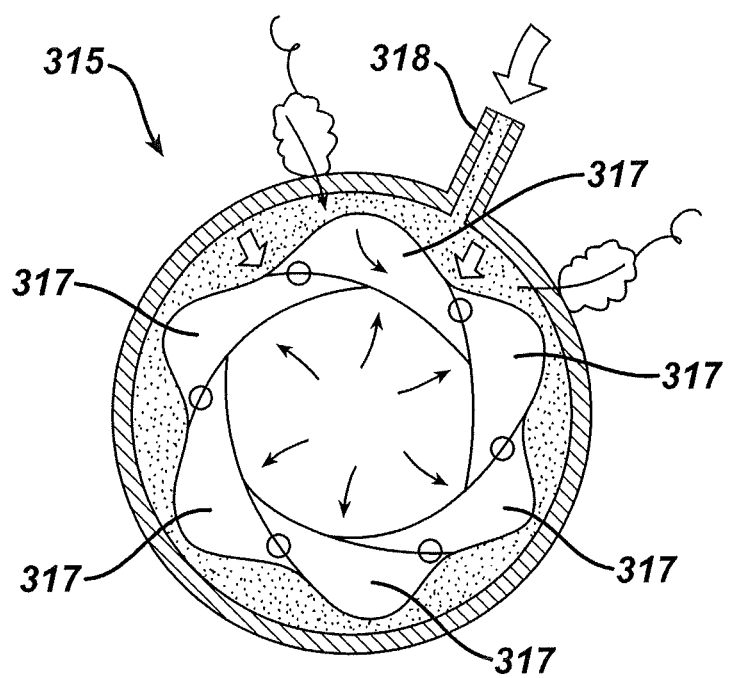
FIG. 35b is a view of the valve of the hybrid band procedure in an opened state.
Figure 35C:
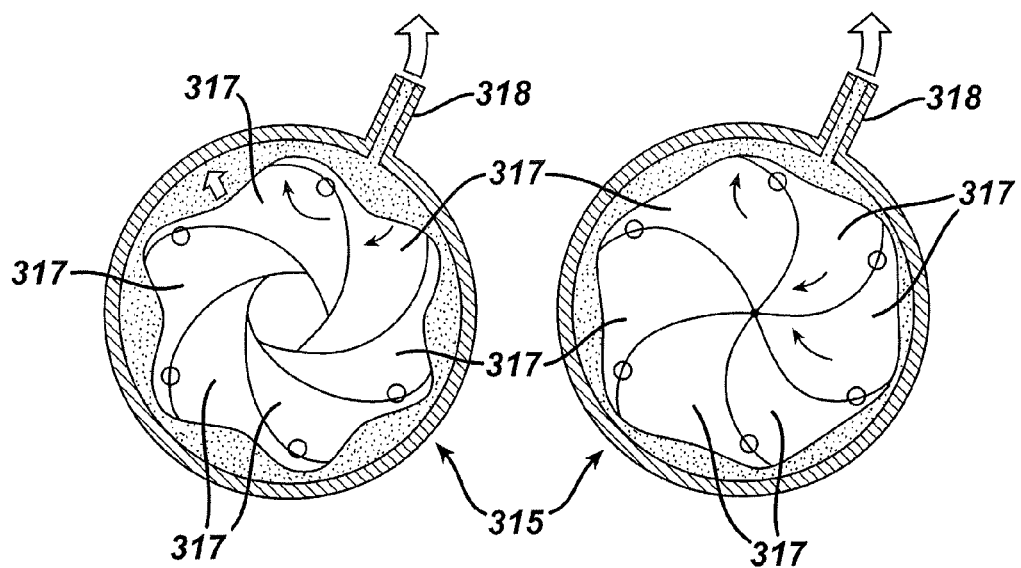
FIG. 35c is a sequential view of the valve of the hybrid band procedure as it closes.

FIG. 35a is a view of the valve 315 of the hybrid band procedure. In this embodiment, the valve 315 is an iris type valve including a body 316 having a port 318. The body 316 supports a plurality of leaves 317 which cooperate to form a sphincter of variable size for permitting material such as chyme to pass. In a preferred embodiment the port 318 is in fluid communication with the tethered gastric band 320 via communications means 325. As shown in FIG. 35b, a pressure applied to port 318 causes each of the leaves 317 to pivot about a hinge point 319 thus dilating the sphincter. Conversely, as is shown in reference to FIG. 35c, a reduction of the pressure applied to port 318 allows the iris to close as will be described in greater detail herein.

Figure 36:
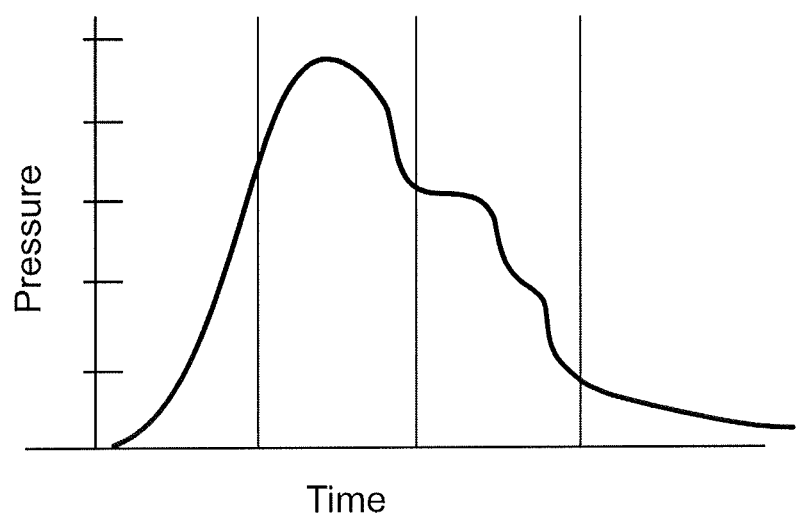
FIG. 36 is a graphic representation of the relationship between the pressure applied to the valve with respect to time.
Figure 37A:
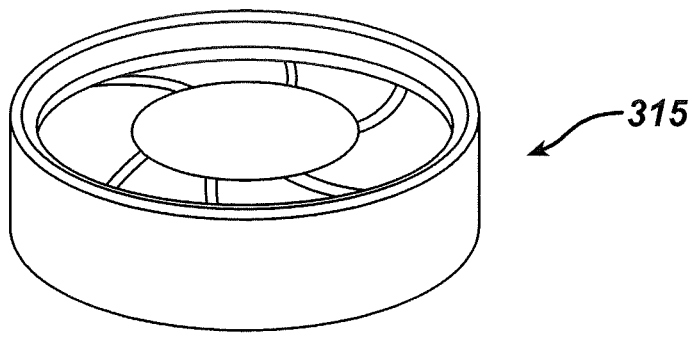
FIG. 37a is the sphincter dilation after one minute.
Figure 37B:
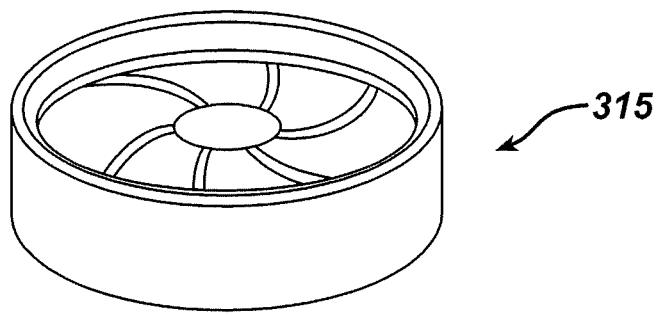
FIG. 37b is the sphincter dilation after five minutes.
Figure 37C:
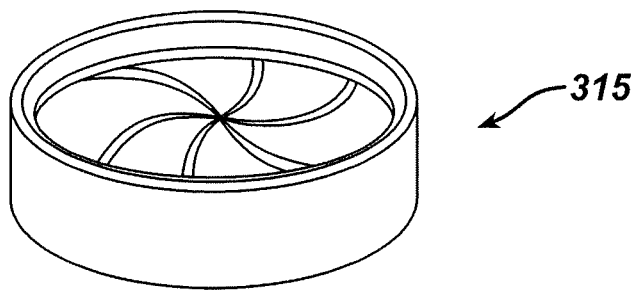
FIG. 37c is the sphincter dilation after ten minutes.

FIG. 36 is a graphic representation of the relationship between the pressure applied to the valve with respect to time. The valve 315 opens for a short period of time after the patient starts eating and then closes for the rest of the meal and does not reset to open again before a minimum of several hours passes. In a preferred embodiment the duration the valve 315 is open is 5 minutes. Alternately, as shown in FIGS. 37a-c the valve 315 slowly closes over a ten minute period with FIG. 37a showing the sphincter dilation after one minute, FIG. 37b showing the sphincter dilation after five minutes and FIG. 37c showing the sphincter dilation after ten minutes. This would also allow some food through to the ileum quickly then leave the rest of the digestive tract undisturbed. The valve 315 may be open for other durations of time without departing from the scope of the present invention.

It is contemplated that the position of the valve 315 can be adjusted to suit particular patient requirements. In one embodiment, the valve 315 is positioned to exit the stomach in the fundus area to accommodate a patient who consumes a high calorie diet in liquid form. The valve 315 would regulate digestion by allowing chyme to exit to the lower GI tract to prevent absorption and to stimulate metabolic affects. Placement of the valve 315 may include alternate positions with the primary function remaining as regulating chyme to prevent absorption.

Figure 38:
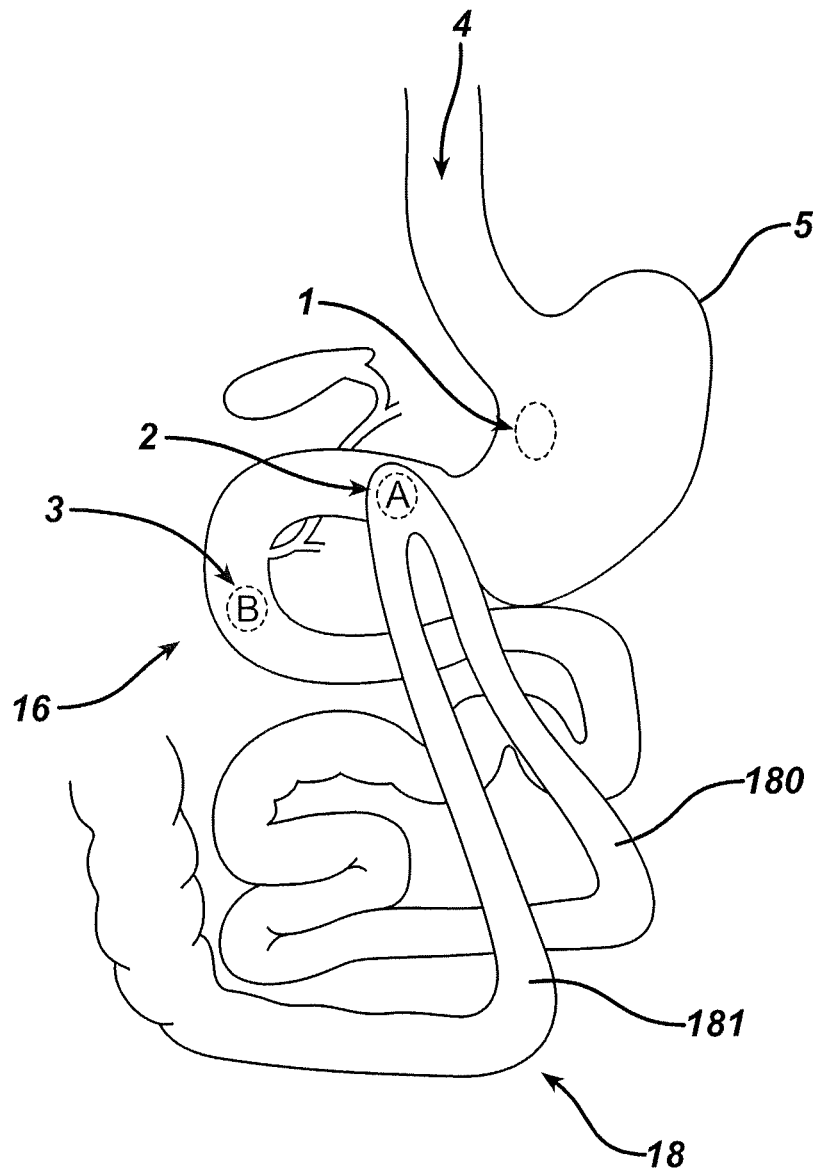
FIG. 38 is a schematic view of a gastrointestinal tract showing anastomosis variants of the hybrid band procedure.

FIG. 38 is a schematic view of a gastrointestinal tract showing anastomosis variants of the hybrid band procedure. In a first embodiment, an anastomosis in the upper sleeve section rather than the jejunum just distal to the pyloric sphincter is indicated at 1 in FIG. 38. In a second embodiment, a jejunum to jejunum anastomosis is mid-length to just above the ileum is shown at 2 in FIG. 38. In a third embodiment, a mid jejunum to CBC bile duct is indicated at 3 in FIG. 38. Further, an anastomosis device may be passed trans-orally as indicated at 4 in FIG. 38 in conjunction with any of the preceding embodiments. It is further contemplated to use the pair of puck anastomosis staples discussed previously.

Figure 39:
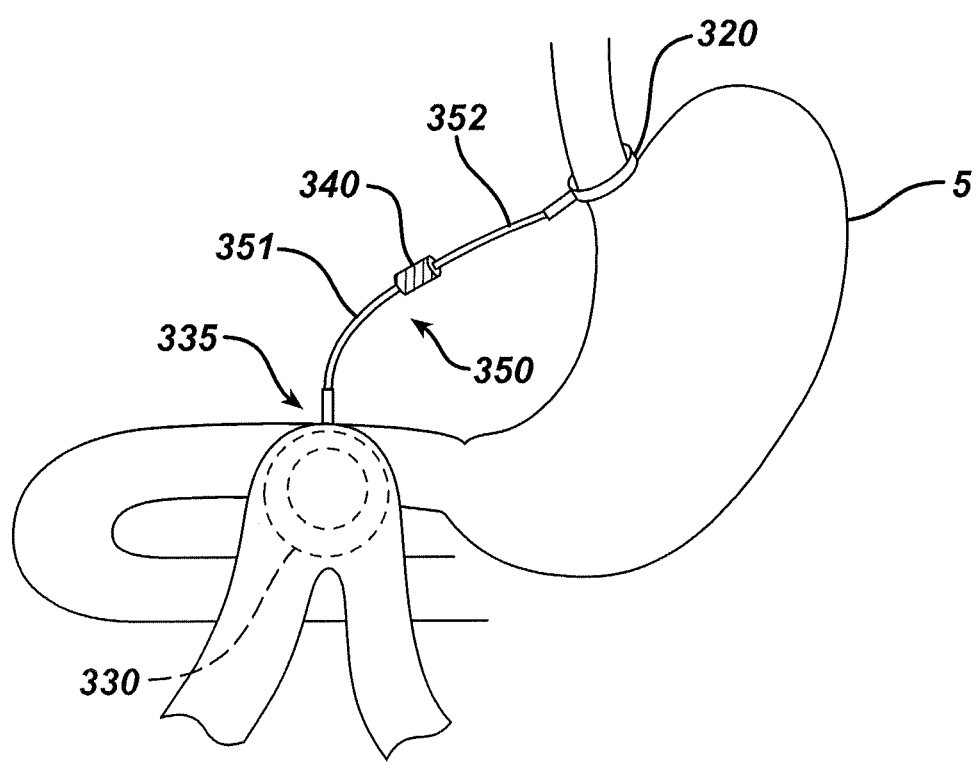
FIG. 39 is a schematic view of a gastrointestinal tract with the tethered gastric band in fluid communication with a second gastric band.
Figure 40A:
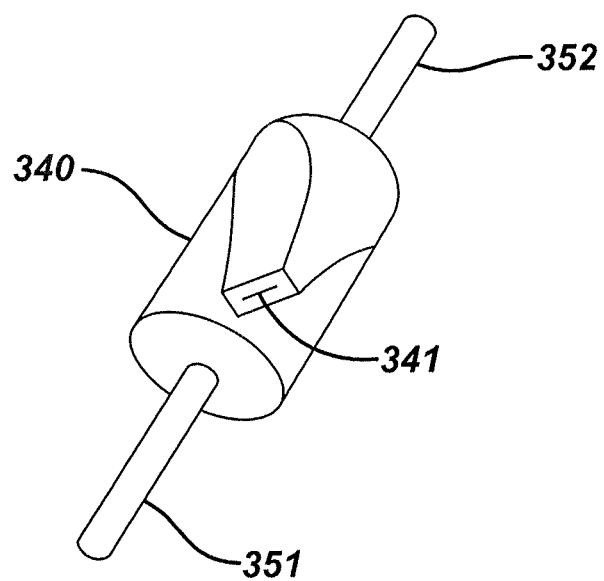
FIG. 40a is a perspective view of a valve.
Figure 40B:
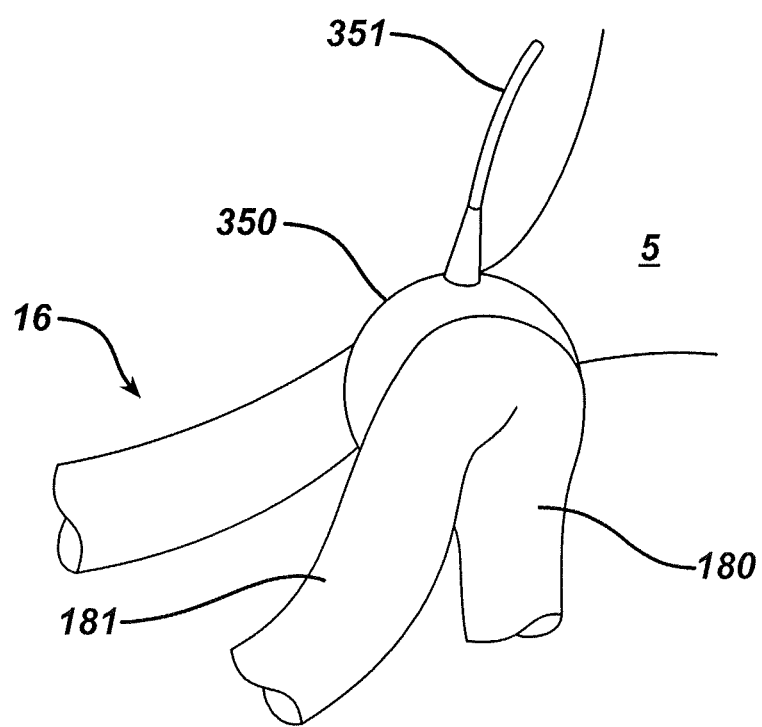
FIG. 40b is a schematic view of a gastrointestinal tract with the tethered gastric band.

FIG. 39 is a schematic view of a gastrointestinal tract with the tethered gastric band 320 in fluid communication with a second gastric band 330. In this particular embodiment the tethered gastric band 320 discussed above could be used in fluid communication with the second gastric band 330 which is wrapped around a duodenal-jejunal anastomosis site 335. The placement of the second gastric band 330 is shown in greater detail in FIG. 40b. The fluid communication is provided by a communications means 350 and regulated by a modified one-way valve 340. Communications means 350 includes a member 351 connecting the modified one-way valve 340 to the second gastric band 330 and a member 352 connecting the modified one-way valve 340 to the tethered gastric band 320. This arrangement would allow rapid flow in the direction from the tethered gastric band 320 to the second gastric band 330 such that peristaltic pressure would begin to transfer fluid from the tethered gastric band 320 to the second gastric band 330. The peristaltic pressure may be, for example, due to the swallowing of food content at the beginning of food consumption. Some food content would have the opportunity to pass through the pylorus before enough fluid passed through to the second gastric band 330 to occlude the anastomosis, thereby forcing all subsequent chyme to pass through the normal channel. The modified one-way valve 340 permits a controlled passage of pressure from the second gastric band 330 toward the tethered gastric band 320. Over time, the modified one-way valve 340 would allow the elasticity of the second gastric band 330 to push the fluid back to the tethered gastric band 320, opening the anastomosis again for the next meal. In a preferred embodiment the modified one-way valve 340 may be a duckbill valve 341 as shown in FIG. 40a. It is contemplated that the diameters of the member 351 and the member 352 may be adjusted in order to tailor fluid communication between the tethered gastric band 320 and the second gastric band 330 through the modified one-way valve 340.

FIGS. 41-44 show alternative embodiments of extraluminal shunts. In these embodiments, an extraluminal shunt is used to direct nutrients from the upper GI tract to desired locations in the lower GI tract. These embodiments use the extraluminal shunt which exits the bowel lumen at the proximal gut and re-enters the bowel lumen in the lower GI tract, preferably the ileum.

Figure 41:
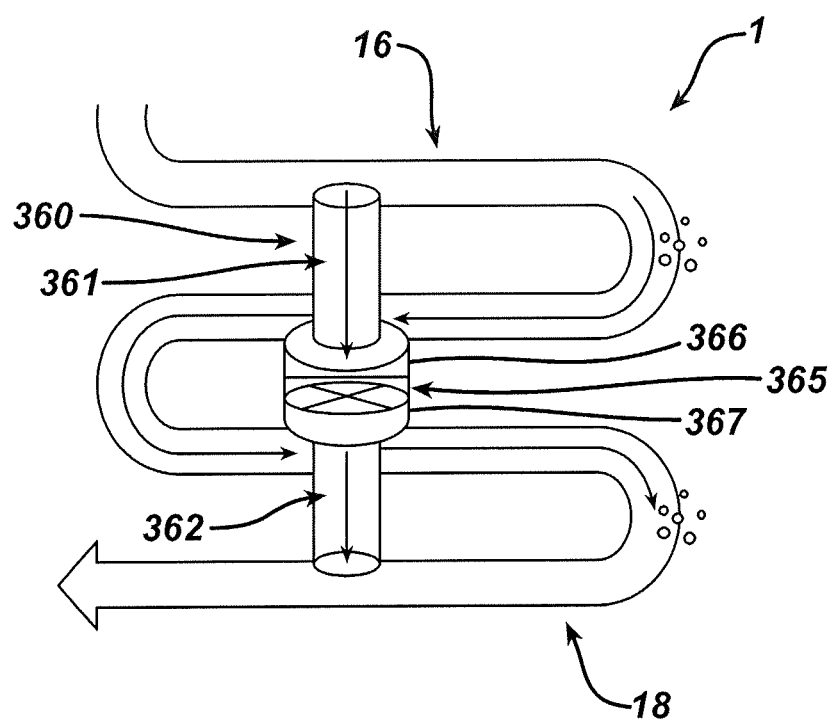
FIG. 41 is a schematic view of a gastrointestinal tract including a shunt including a storage area.

FIG. 41 is a schematic view of a gastrointestinal tract 1 including a shunt 360 including a storage area 365. The shunt 360 including establishes fluid communication between the duodenum 16 and the ileum 18. A first portion 361 provides fluid communication between the duodenum 16 and the storage area 365. A second portion 362 provides fluid communication between the storage area 365 and the ileum 18. In a preferred embodiment the storage area 365 is divided into two chambers, an upper chamber 366 and a lower chamber 367.

The shunt 360 may include a buffer substance that is eluded into the chyme as it passes through the shunt 360 to permit ileal brake induction without damage to the proximal bowel due to acidic pH of the chyme. The chyme entering the shunt 360 from the proximal bowel with a low pH will exit the shunt 360 at the desired location at a neutral pH in order to initiate the ileal brake. It is contemplated that the buffer substance could be resupplied to the extraluminal shunt by a fill port. Further, the buffer substance could simply saturate the internal lining of the shunt as an alternative to elution as a mechanism of buffering. In one embodiment, such a buffer substance could be calcium carbonate.

The upper chamber 366 acts as a reservoir for a portion of mechanically and chemically broken down food or chyme received from the duodenum 16 through the first portion 361. When large amounts of food are consumed the shunt 360 carries the bulk of it away and prevents absorption while slowly releasing it into the distal ileum 18 at a controlled rate. Further, it is contemplated that a pump may be included to ensure the chyme passes through the shunt 360 without clogging. The stored chyme would remain in the upper chamber until the initiation of the next meal, at which time; it would be transferred to the lower chamber 367 through the second portion 362 and to the ileum 18 at a controlled rate. In one embodiment, initiation of chyme transfer between the upper chamber 366 and the lower chamber 367 is accomplished using a chamber release trigger. The chamber release trigger could be set via exogenous mechanisms such as telemetric means or by an implanted mechanism. It is contemplated that the beginning of a meal be used as an initiation point for the chamber release trigger. An alternative embodiment contemplates using a valve-like or pump-like release mechanism as used in other implantable devices.

The presence of chyme in the ileum 18 activates the intestinal brake response and leads to reduction in hunger and food intake. The remainder of the chyme passes through the gastrointestinal tract 1 as indicted by the arrows on FIG. 41. The upper chamber 366 will then be empty and ready to store new chyme from the duodenum 16 to be release at the start of the next meal. An advantage of the present embodiment is the utilization of a more natural stimulator of the ileal brake response as an alternative to electronic or mechanical stimulations. In one embodiment, it is contemplated that the shunt 360 could be made of biocompatible materials.

Figure 42:
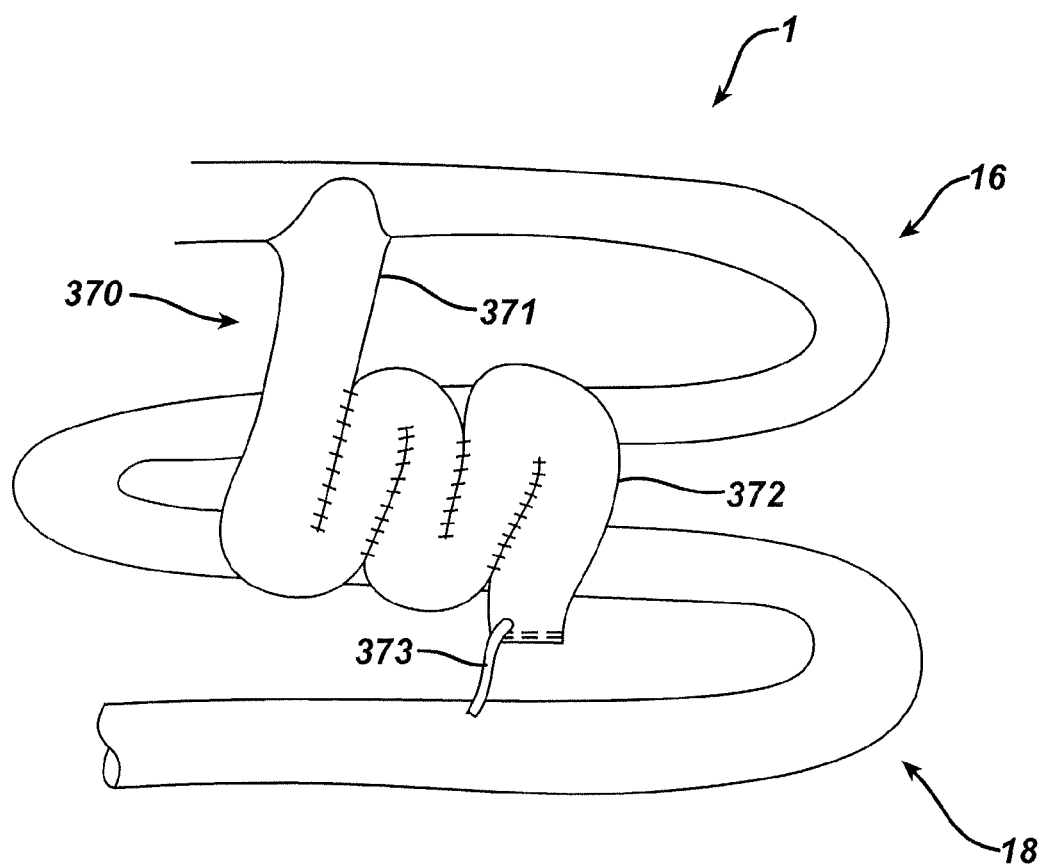
FIG. 42 is a schematic view of a gastrointestinal tract including a shunt.

FIG. 42 is a schematic view of a gastrointestinal tract 1 including a shunt 370. In this embodiment, the shunt 370 includes a bypass 371 and a reservoir 372 which have been realized in a biologically compatible fashion by constructing the bypass 371 and reservoir 372 from autologous tissue. Preferably, the shunt 370 is constructed from a segment of jejunum. The segment of jejunum is moved from its original location with mesentery still attached and reconstructed to form the bypass 371 and reservoir 372. The distal end of the apparatus may be reduced in diameter by using a smaller vessel 373 attached to the ileum 18. In a preferred embodiment the vessel 373 is a necked down portion of jejunum or other intestine. Alternatively the vessel 373 is formed using a harvested portion of another vessel such as, for example, a saphenous vein.

The shunt 370 may include a buffer substance that is eluded into the chyme as it passes through the shunt 370 to permit ileal brake induction without damage to the proximal bowel due to acidic chyme. The chyme entering the shunt 370 from the proximal bowel with a low pH will exit the shunt 370 at the desired location at a neutral pH in order to initiate the ileal brake. It is contemplated that the buffer substance could be resupplied to the extraluminal shunt by a fill port. Further, the buffer substance could simply saturate the internal lining of the shunt as an alternative to elution as a mechanism of buffering. In one embodiment, such a buffer substance could be calcium carbonate.

Figure 43A:
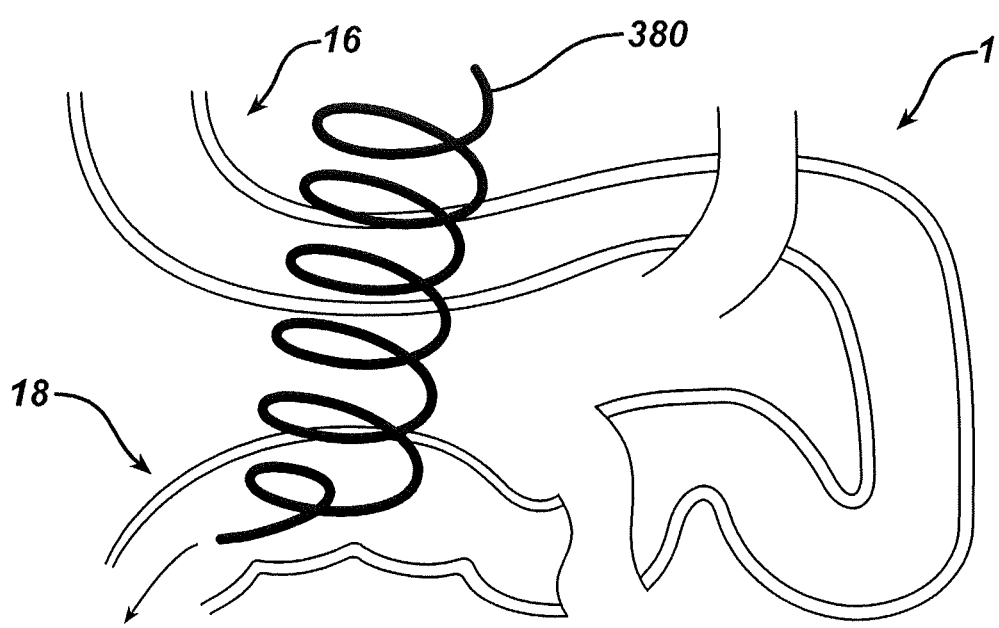
FIG. 43a is a schematic view of a gastrointestinal tract including a coiled shunt tube.

FIG. 43a is a schematic view of a gastrointestinal tract 1 including a coiled shunt tube 380. In this embodiment, the coiled shunt tube 380 provides a flexible path between the proximal and distal gut. Advantageously, the flexible nature of the coiled shunt tube 380 would help prevent excess stress on the tissue attachment points due to body movement. The length of the coiled shunt tube 380 provides a reservoir effect as described above with respect to the embodiments of FIGS. 41 and 42. Further, the coiled shunt tube 380 includes a one way valve as described herein. The valve may placed at any suitable point in the coiled shunt tube 380.

Figure 43B:
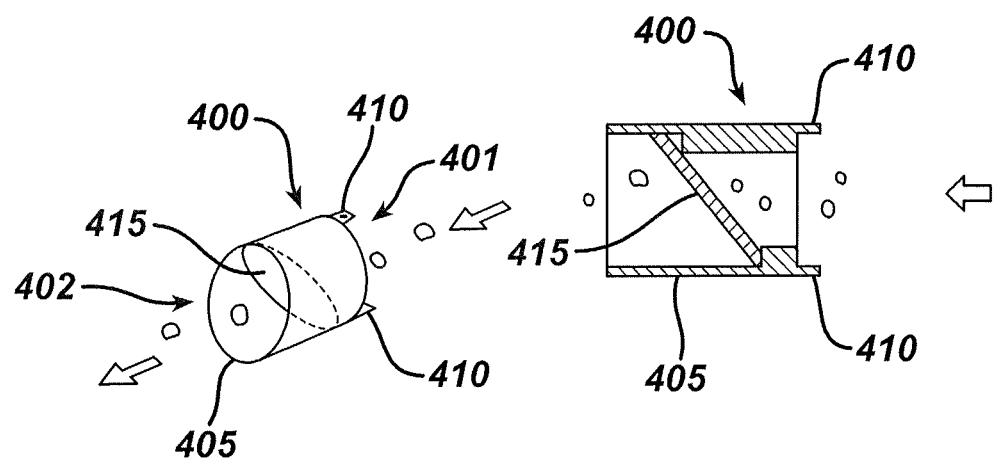
FIG. 43b is a perspective view of a one way valve and a cut away view of the one way valve.

FIG. 43b is a perspective view of a one way valve 400 and a cut away view of the one way valve 400. The one way valve 400 includes a valve body 405 having a proximal end 401 and a distal end 402. A first suture tab 410 and a second suture tab 410 project from the proximal end 401 of the valve body 405. The valve body 405 houses a flapper 415 which only permits flow through the valve body 405 from the proximal end 401 to the distal end 402 as indicated by the arrows.

Figure 43C:
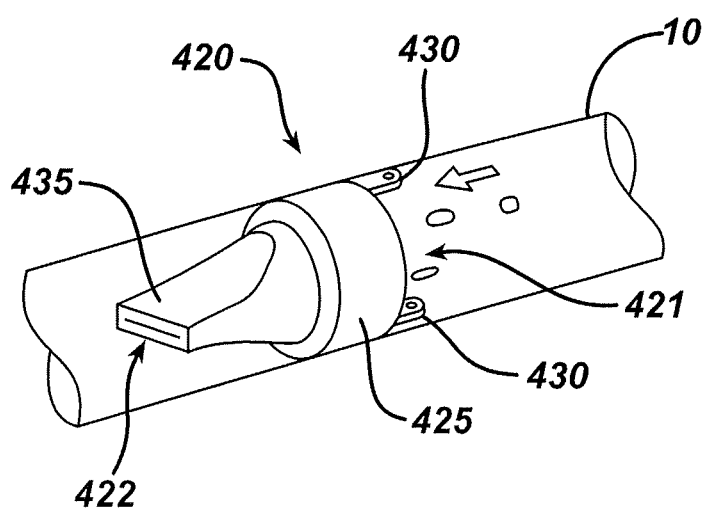
FIG. 43c is a perspective view of an alternative embodiment of a one way valve after placement in a bowel.

FIG. 43c shows a perspective view of an alternative embodiment of a one way valve 420 after placement in a bowel 10. In this embodiment, the one way valve 420 includes a valve body 425 having a proximal end 421 and a distal end 422. A first suture tab 430 and a second suture tab 430 project from the proximal end 421 of the valve body 425. The one way valve 420 includes a valve portion 435. Fluid pressure acting on the valve portion 430 permits flow from the proximal end 421 to the distal end 422 through the valve body 425. Preferably the valve portion 430 is formed of a pliable material such as, for example, rubber.

Another embodiment of an extraluminal shunt includes a pumping system. The pump with the extraluminal shunt transfers nutrients to the ileum at a desired rate due to the pump. The result is that earlier ileal brake inducement is made possible. The pump allows for the delivery of nutrients to the ileum according to a predetermined beneficial schedule. This provides a less invasive alternative to ileal transposition.

In a preferred embodiment, the pumping system includes at least four subsystems: a shunt subsystem, pump subsystem, a sensing subsystem and a power generation and storage subsystem. It is contemplated that the shunt subsystem be any of the embodiments disclosed herein. It is further contemplated that the pump subsystem is comprised of any implantable or external pumping means such as, for example, single or multiple fluid pumps, piezoelectric actuated pumps, osmotic pumps or MEMS pumps. The sensing subsystem may be based on any suitable sensing or measuring means such as, for example, displacement, pressure, pH or glucose.

A temperature based sensing means may be triggered if the temperature of the stomach contents is above or below a threshold. Alternately, the sensor may trigger if a patient drinks a sequence of hot and/or cold drinks before eating. One contemplated displacement sensing means includes, for example, a piezofilm secured to the fundal region of the stomach either intragastrically or on the serosal layer. The piezofilm generates an electric current when flexed thus signalling or measuring gastric motility or gastric pressure. As may be appreciated, this film can be attached to other upper GI members such as duodenum, jejunum or even subcutaneously to provide for user actuation. Pressure may be intra gastric or outside the body as applied by the patient via an external or subcutaneous device.

It is contemplated that displacement sensing means includes motion detection. In one embodiment the, motion may be detected by an accelerometer, gravitometer, inclinometer or other suitable motion measuring device. Motion detection may occur during various time periods such as, for example, during the day with motion detection inactive at night.

The power subsystem may a wearable power source. Non-limiting disclosures of a wearable power source can be found in U.S. patent application Ser. No. 11/958,638, filed Dec. 18, 2007, entitled Wearable Elements For Implantable Restriction Systems, in U.S. patent application Ser. No. 12/027,820, filed Feb. 7, 2008, entitled Powering Implantable Restriction Systems Using Kinetic Motion, in U.S. patent application Ser. No. 12/027,817, filed Feb. 7, 2008, entitled Powering Implantable Restriction Systems Using Temperature, and in U.S. patent application Ser. No. 12/027,784, filed Feb. 7, 2008, entitled Powering Implantable Restriction Systems Using Light, which are hereby incorporated by reference in their entirety.

Figure 44:
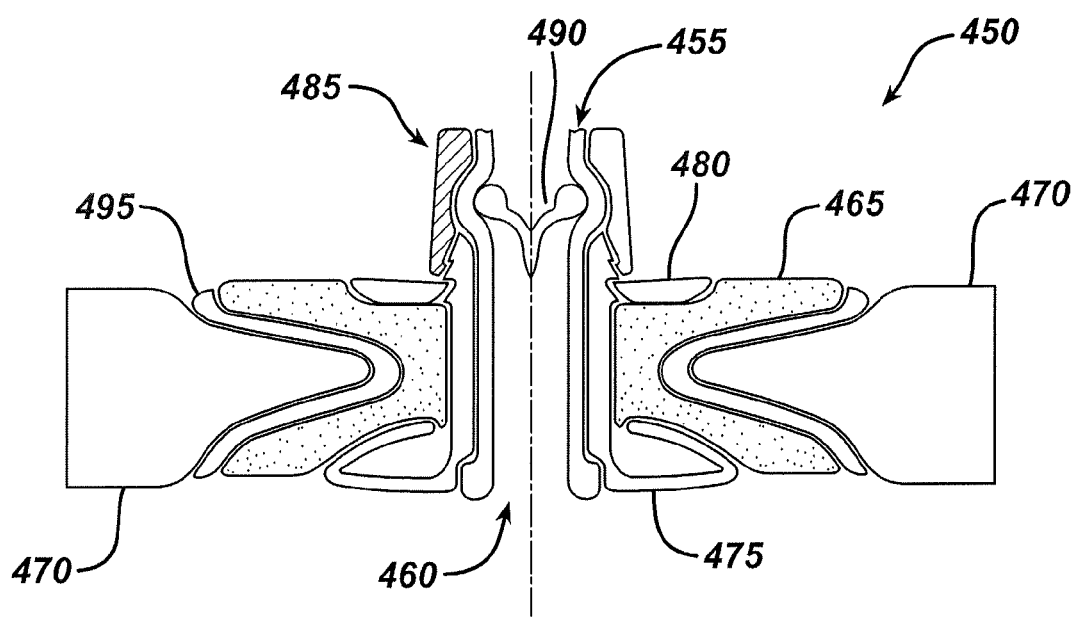
FIG. 44 is a cross sectional view of a laproscopically delivered lumen port.

FIG. 44 is a cross sectional view of a laproscopically delivered lumen port 450. In this embodiment, the lumen port 450 provides a direct physical connection between a subcutaneous port directly to the interior of a lumen such as an ileum or duodenum. The direct physical connection is similar to the gastric band described herein. The lumen port 450 includes a tube 455 defining a lumen 460. The tube 455 may be an extraluminal shunt as described herein. A seal 465 surrounds the tube 455 and is held in place by a guide retainer 475 which couples with a retainer 480 to surround seal 465 and secure it in position. A ring 485 is disposed about the tube 455 and the guide retainer 475. A valve 490 is disposed within the tube 455 to permit fluid communication in one direction through tube 455. It is contemplated that valve 490 may be any of the embodiments disclosed herein. The lumen port 450 may be made of any suitable material with out departing from the scope of the present invention. It is further contemplated that a portion or all of the lumen port 450 is conductive.

In a preferred embodiment the seal 465 is made of an elastomeric material. Further, a sealing means 495 such as a tissue sealant may be disposed between the seal 465 and the lumen wall 470. Further it is contemplated that the lumen port 450 is surrounded at the tissue contact interface by a material which may be quickly endothelialized. It is contemplated that such materials include hernia mesh materials or functionalized keratin sheets. Such a material would encourage tissue growth up to the boundary of the implant device to prevent thrombosis.

The lumen port 450 can be laproscopically delivered and provides a means to deploy therapies such as, for example, a targeted therapy to stimulate GLP-1 or administering a liquid or gel application via endoscopic delivery. It is further contemplated that the therapy includes delivery of modified cells to the ileum or duodenum. The lumen port 450 provides a means to sense internal conditions such as sensing hormonal response. Further, the lumen port 450 provides a lumen to lumen connection such as the duodenum to ileum for more direct immediate physical communication in order to stimulate GLP-1.

It is further contemplated that the lumen port 450 be used to provide an exposed external port. Such a port would provide a direct connection via a transdermal patch. Further, the port could be connected to an implantable infusion pump system that regulates delivery of a substance to the area being stimulated. The lumen port 450 may have other placements without departing from the scope of the present invention.

In one embodiment, the lumen port 450 has on-board sensing and an electrical connection to the subcutaneous port to permit the transmission of information. Contemplated transmission means include wireless and optical means. Further, the lumen port includes an electrode configuration or an array of electrodes that can be connected to an electrical stimulation device. In another embodiment the lumen port 450 system includes an electromagnetic coil around the tube 455, and the coil could be energized from a distance from the port either internal or external to the body. The coil could be tuned to a specific resonant frequency to achieve the desired stimulation signal.

Additionally, it is contemplated that the connection can be associated with a reservoir and pump to feed into the lumen access. The connection can be internal or external and the reservoir can be a disposable or refillable type. The pump may be an automatic or manual type as disclosed herein.

Figure 45:
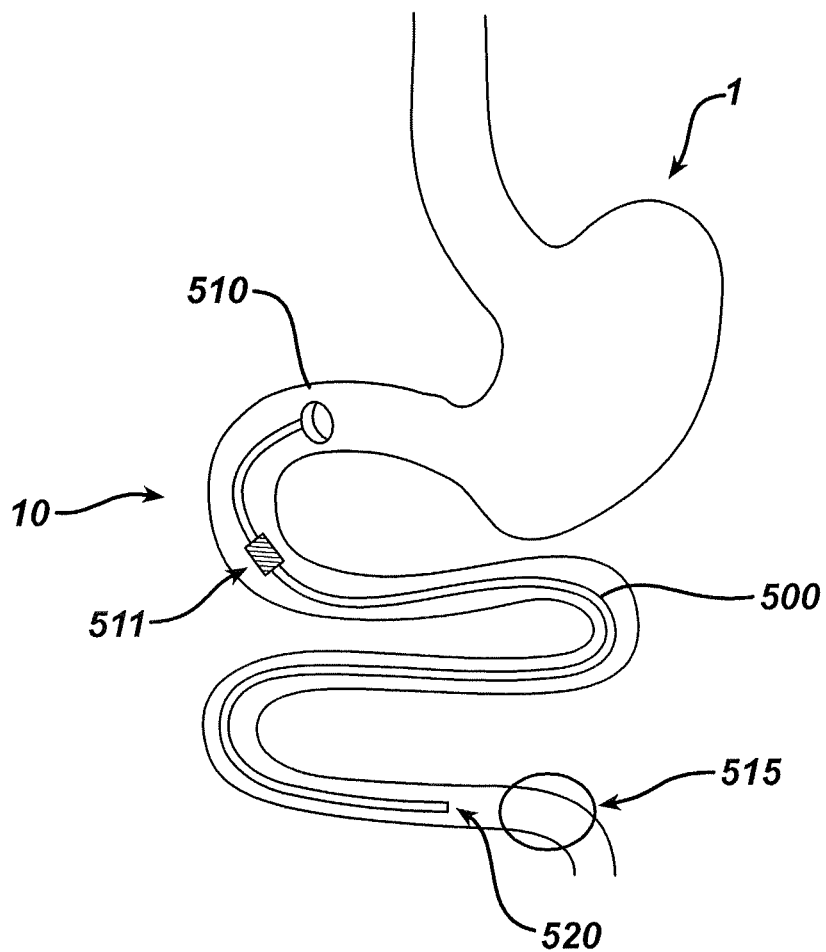
FIG. 45 is a schematic view of a gastrointestinal tract including an intraluminal shunt with one exit and one target region.

FIG. 45 is a schematic view of a gastrointestinal tract 1 including an intraluminal shunt 500 with one exit 520 and one target region 515. In this embodiment, the intraluminal shunt 500 includes a proximal end 510 and a distal end 520. The intraluminal shunt 500 provides a path through the bowel 10 for chyme from the proximal end 510 to a desired target location 515 or locations near the distal end 520 in the distal bowel 10. The intraluminal shunt 500 prohibits nutrient absorption of the chyme by the bowel as the chyme passes through the shunt 500. This shielding effect provides chyme that is more nutrient rich to the distal bowel 10, which is more likely to stimulate the intestinal brake. Further, a one way valve 511 may be disposed on the shunt 500 between the proximal end 510 and the distal end 520. Further, any optional subsystem may be placed between the proximal end 510 and the distal end 520 such as, for example, pumps or sensors as described herein.

Figure 46:
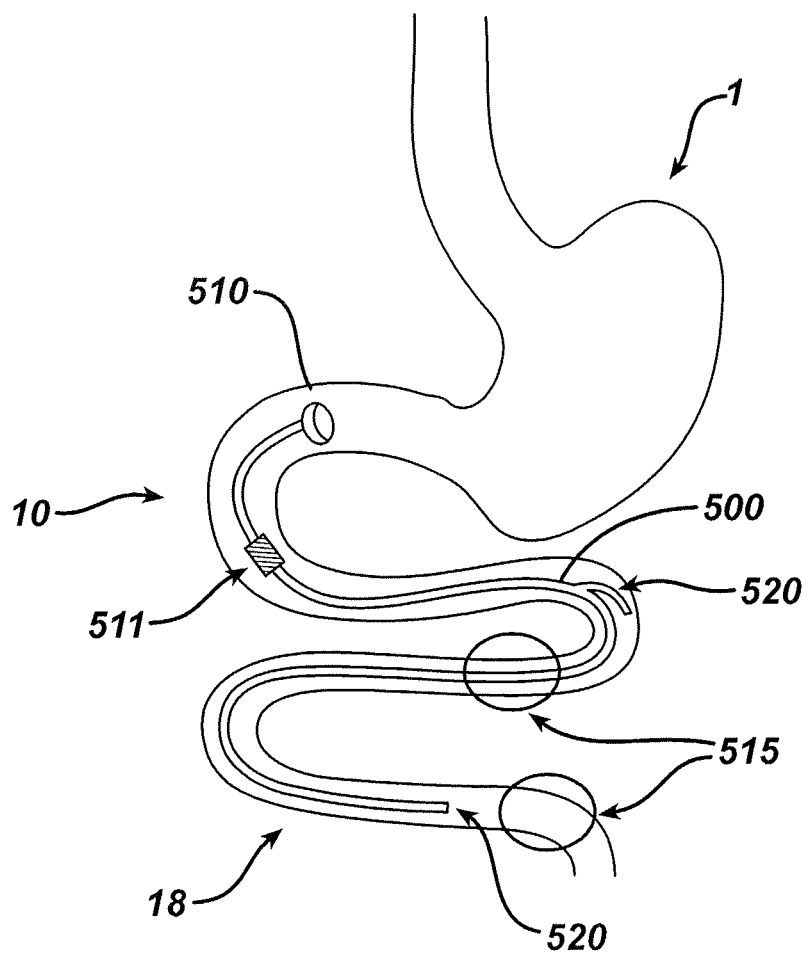
FIG. 46 is a schematic view of a gastrointestinal tract including an intraluminal shunt with multiple exits and target regions.

FIG. 46 is a schematic view of a gastrointestinal tract 1 including an intraluminal shunt 500 with multiple exits 520 and target regions 515.

Figure 47:
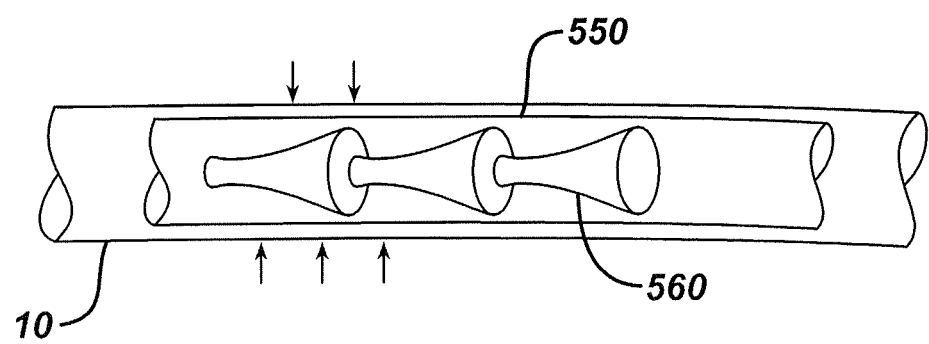
FIG. 47 is a schematic view of a shunt including stent segments.

FIG. 47 is a schematic view of a shunt 550 including stent segments 560. In this embodiment, the stent segments 560 are advantageously constructed to amplify peristalsis such that each contraction of the stomach will result in a further excursion of the chyme along the shunt 550 than would normally be experienced in the intestine.

Figure 48:
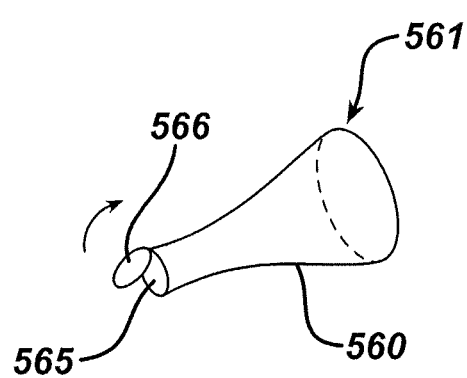
FIG. 48 is perspective view of one of the stent segments.

FIG. 48 shows perspective view of one of the stent segments 560. The stent segments 560 are progressively necked down to an aperture 565 so as volume of the segment is reduced by peristalsis; chyme must accelerate to move through the aperture similar to a nozzle effect. It is contemplated that the proximal end of the segment 561 would be fixed to the wall of the shunt 550 for stability using an anchor. Further, each of the stent segments 560 may also include a one way valve to prevent backflow of chyme. In a representative embodiment, the one way valve would be a flapper valve 566.

In a preferred embodiment, the anchor for the shunt may be a laser cut or woven wire stent which is fastened to the lumen wall by suture, t-tags or by tissue overgrowth in the case of an expanding stent. Further, barbs on the stent may serve to fasten the stent to the wall of the intestine. The anchor may have other forms without departing from the scope of the present invention. It is contemplated that the inflatable shunt anchor described with respect to FIG. 33 is used to anchor the shunt 550 as described herein. The shunt may be sized so as to conduct all or a portion of the intestinal content (chyme) to the distal region. Further, the internal surface of the shunt may be coated with a lubricious material such as a hydro gel to facilitate quicker passage of the content to the distal gut.

Figure 49:
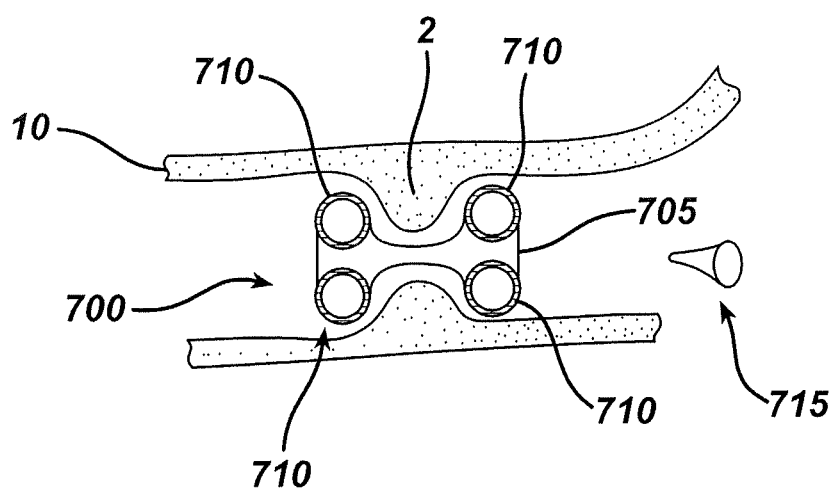
FIG. 49 is a schematic view of a section of bowel following the implantation of an inflatable shunt anchor.

FIG. 49 is a schematic view of a section of bowel 10 following the implantation of an inflatable shunt anchor 700. The inflatable shunt anchor 700 is anchored to the intestinal wall by inserting a tube 705 through the pylorus 2 and then inflating balloons 710 on both sides of the pylorus 2, preventing forward or reverse motion of the inflatable shunt anchor 700 with respect to the pylorus 2. Further, the entire assembly may be substantially flexible such that it flexes with pyloric contractions, but preferably always remains larger than the pyloric opening. It is contemplated that the inflatable shunt anchor 700 may also be advantageously anchored with a stent fixed to the bowel wall by barbs, suture or t-tags. Further, it is contemplated that the inflatable shunt anchor 700 may include a one way valve 715 as described herein.

Figure 50:
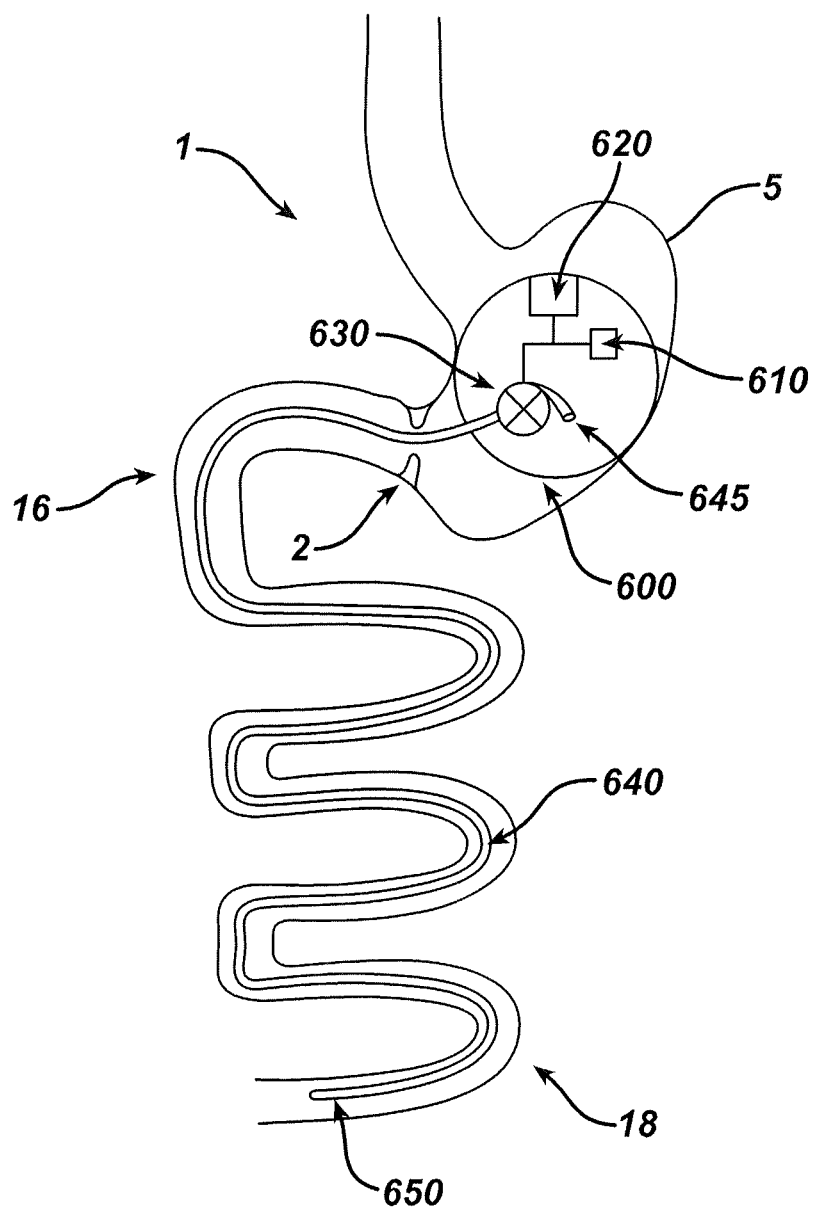
FIG. 50 is a schematic view of a gastrointestinal tract including a dynamically adjustable belly ball.

FIG. 50 is a schematic view of a gastrointestinal tract 1 including a dynamically adjustable belly ball 600. In this embodiment, the presence or anticipation of food in the stomach 5 causes certain physiological changes such as, for example, a lowering of pH, that are sensed by a sensor 610 attached to the belly ball 600. The sensor 610 is in communication with ball expansion motor 620, which in turn causes the ball to expand. The sensor 610 is also in communication with a pump 630 which is in fluid communication with the ileal brake accelerator tube 640 which has a proximal end 645 and a distal end 650 located in the ileum 18. Sensor 610 also causes the pump 630 in the belly ball 600 to advance a portion of the chyme contained in the stomach 5 through the proximal end 645 and directly to the ileum 18. It is further contemplated that between meals, the pump 630 could continue to meter chyme input to the ileum on a slow continual or periodic basis in order to maintain and prolong satiety. The chyme may be drawn from a cache of chyme held in the belly ball 600. The chyme may be stored in other forms and placements without departing from the scope of the present invention. Further, the shape of the ball 600 could be non-spherical so that it maintains orientation, and its expansion could be asymmetric to tailor the expansion effects to various targeted regions of the stomach.

In an alternate embodiment, the stent segments as disclosed herein include a means to accelerate the action of the body's ileal brake mechanism to achieve a complete solution for causing early onset of satiation and prolonged satiety. It is contemplated that the means to accelerate the action of the body's ileal brake mechanism include the stent segments as described herein.

Alternate embodiments could involve pumping something other than the raw chyme to the ileum. A first alternate embodiment includes pumping biologics that are produced in vivo by filtering, processing, or converting the chyme within the belly ball 600 to create the substance that is pumped, or pumping a substance from a closed, refillable reservoir within the belly ball 600. Refilling of the reservoir may be accomplished while the reservoir is in vivo such as, for example, through the esophagus. It is contemplated that processing may be accomplished using a lab-on-a-chip. Further, the substance may include a biologic or therapeutic substance.

Further, it is contemplated that one or more of many input signals within the body could be used to control the pump 630 and expansion of the ball 600. In one alternate embodiment, the portion of the tube 640 that passes through the pyloric sphincter 2 could made rigid enough that it would not be crushed or pinched off when the sphincter is closed, or it may be made flexible enough that it would normally be pinched off when the sphincter is closed, and only open when the sphincter is open, or when pressure from the pump forces it open. Power for the devices in the belly ball 600 could be stored and recharged periodically, or could be provided by energy converted from its surroundings. The power may be provided by a wearable power source.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

We claim:

1. A method for rerouting chyme to induce an intestinal brake, the method comprising the steps of:
   a. accessing a gastrointestinal tract of a patient; and
   b. performing a procedure that shortens a digestive path within the gastrointestinal tract to induce the intestinal brake, wherein the procedure comprises the steps of:
      i. passing a suture through an outer layer of a bowel of the patient in an alternating fashion, and
      ii. drawing ends of said suture into a knot, said step of drawing forming a tight loop causing said bowel to bunch along said suture, wherein said step of drawing ends of said suture into a knot causes a length of said bowel to shorten.

2. The method of claim 1 wherein said method does not include surgical removal of any portion of the bowel.

3. The method of claim 2 wherein said step of accessing is carried out using a flexible endoscope outfitted with a stitching device.

4. The method of claim 1 wherein said step of passing a suture comprises passing more than one suture.

5. The method of claim 1 wherein said procedure that shortens the digestive path is reversible.

* * * * *